(12) United States Patent
Salli et al.

(10) Patent No.: US 7,754,483 B2
(45) Date of Patent: Jul. 13, 2010

(54) SYSTEMS AND METHODS FOR SELECTION AND MAINTENANCE OF HOMOGENEOUS AND PLURIPOTENT HUMAN EMBRYONIC STEM CELLS

(75) Inventors: Ugur Salli, Hummelstown, PA (US); Mark Kester, Harrisburg, PA (US); Kent E. Vrana, Hummelstown, PA (US)

(73) Assignee: The Penn State Research Foundation, University Park, PA (US)

( * ) Notice: Subject to any disclaimer, the term of this patent is extended or adjusted under 35 U.S.C. 154(b) by 566 days.

(21) Appl. No.: 11/557,791

(22) Filed: Nov. 8, 2006

(65) Prior Publication Data

US 2007/0111306 A1   May 17, 2007

Related U.S. Application Data

(60) Provisional application No. 60/734,862, filed on Nov. 9, 2005.

(51) Int. Cl.
  *C12N 5/00*  (2006.01)
(52) U.S. Cl. .................. 435/377; 435/325; 435/375
(58) Field of Classification Search .................. None
  See application file for complete search history.

(56) References Cited

U.S. PATENT DOCUMENTS

2005/0025820 A1   2/2005   Kester et al.

FOREIGN PATENT DOCUMENTS

| WO | WO 00/15764 | * | 3/2000 |
| WO | WO 2004/029203 A2 | * | 4/2004 |

OTHER PUBLICATIONS

Sumi T et al. 2007. Apoptosis and differentiation of human embryonic stem cells induced by sustained activation of c-Myc. Oncogene 26: 5564-5576.*

Ginis I et al. 2004. Differences between human and mouse embryonic stem cells. Dev Biol 269: 360-380.*

Salli U et al. 2009. Propagation of undifferentiated human embryonic stem cells with nano-liposomal ceramide. Stem Cells Devel 18: 55-65.*

Bieberich, E., J. Silva, G. Wang, K. Krishnamurthy, and B.G. Condie. "Selective apoptosis of pluripotent mouse and human stem cells by novel ceramide analogues prevents teratoma formation and enriches for neural precursors in ES cell-derived neural transplants." The Journal of Cell Biology, vol. 167, No. 4, Nov. 22, 2004. p. 723-734.

Bieberich, E., T. Kawaguchi, and R.K. Yu. "N-Acylated Serinol is a Novel Ceramide Mimic Inducing Apoptosis in Neuroblastoma Cells." The Journal of Biological Chemistry, vol. 275, No. 1, Jan. 7, 2000. p. 177-181.

Bieberich, E., S. MacKinnon, J. Silva, and R.K. Yu. "Regulation of Apoptosis during Neuronal Differentiation by Ceramide and b-Series Complex Gangliosides." The Journal of Biological Chemistry, vol. 276, No. 48, Nov. 30, 2001. p. 44396-44404.

T. Herget, C. Esdar, S. Oehrlein, M. Heinrich, S. Schutze, A. Maelicke, G. van Echten-Deckert, "Production of Ceramides Causes Apoptosis During Early Neural Differentiation in Vitro," Journal of Biological Chemistry, vol. 275, No. 39, Sep. 2000, pp. 30344-30354.

* cited by examiner

*Primary Examiner*—Lora E Barnhart
(74) *Attorney, Agent, or Firm*—Gifford, Krass, Sprinkle, Anderson & Citkowski, P.C.

(57) ABSTRACT

A number of human disorders are characterized by degeneration or loss of specific cells, resulting in pathology associated with reduction or absence of cell function. Such diseases include neurodegenerative diseases and diabetes. Methods are described for obtaining a substantially homogeneous population of undifferentiated human embryonic stem cells including incubating a population of human embryonic stem cells with an amount of a selection agent. The selection agent is effective to reduce or eliminate differentiated embryonic stem cells from the population of cells such that a substantially homogeneous population of undifferentiated human embryonic stem cells is obtained. The substantially homogeneous population of undifferentiated embryonic stem cells may be produced without use of feeder cells.

8 Claims, No Drawings

SYSTEMS AND METHODS FOR SELECTION AND MAINTENANCE OF HOMOGENEOUS AND PLURIPOTENT HUMAN EMBRYONIC STEM CELLS

CROSS-REFERENCE TO RELATED APPLICATIONS

This application claims priority to U.S. Provisional Application Ser. No. 60/734,862, filed Nov. 9, 2005, the entire content of which is incorporated herein by reference.

FIELD OF THE INVENTION

The present invention relates generally to methods and compositions for producing and maintaining undifferentiated embryonic stem cells without substantial contamination by differentiated cells and/or feeder cells. In particular, the present invention relates to methods and compositions for producing and maintaining undifferentiated human embryonic stem cells without substantial contamination by differentiated cells and/or feeder cells.

BACKGROUND OF THE INVENTION

A number of human disorders are characterized by degeneration or loss of specific cells, resulting in pathology associated with reduction or absence of cell function. Such diseases include neurodegenerative diseases and diabetes.

The incidence of neurodegenerative diseases, including Alzheimer's, Parkinson's and motor neuron diseases, have tripled in the last 20 years (Pritchard C, et al., Public Health, 2004 118:268-283). Given the aging population, it has been estimated that there will be more than 100 million people worldwide affected with Alzheimer's disease alone by 2050 (Scorer C A., Drug Discov. Today, 2001 6:1207-1219). These central nervous diseases are irreversible and characterized by the progressive loss of neurons.

Similarly, diabetes affects an increasing number of people. Currently over 18 million Americans suffer from this disease. Approximately 5 to 10% of the diabetes patients are Type 1 diabetics affecting mostly children and young adults. Type 1 diabetes is an autoimmune disease that irreversibly destroys the insulin-producing beta-cells that constitute up to 80% of the pancreatic islets.

Current treatments for diseases characterized by cell loss and/or reduction in normal cell function include exogenous administration of cell products, such as insulin in the case of diabetes. However, such treatment is expensive and fraught with complications. Further, no effective treatment exists for patients suffering from neurodegenerative diseases because neuronal regeneration in the central nervous system is limited and/or compromised in these patients.

Embryonic stem cells are a possible tool for replacement of diseased or lost cells. In addition, stem cells potentially provide valuable research and drug screening tools. However, there are currently significant limitations associated with these cells. In particular, the cells have tremendous plasticity, possessing multiple independent differentiation pathways (Filip S, et al., J Cell Mol Med., 2004 8:572-7). As a consequence, some of these cells undergo spontaneous and premature differentiation in culture, resulting in heterogeneous populations of cells, that is, populations containing some undifferentiated cells and some differentiated cells. Further, differentiated cells themselves may be heterogeneous in such a culture, having mixed lineage.

Use of a heterogeneous population of stem cells as starting material in a process directed to producing differentiated cells is disadvantageous since only a limited number of a desired type of differentiated cell can be produced from such a starting material.

However, obtaining desired cell types in sufficient quantities is not the only obstacle to efforts to develop stem cell replacement therapeutics and research tools. For example, prior to potential transplants, strict screening of the transplant material for contamination of undifferentiated or partially differentiated cells is currently required to prevent formation of stem cell-derived tumors (teratomas). Further, use of differentiated stem cells as drug screening tools may be of limited use where mixed populations of cells are present, since less than optimal signal to noise ratios may be obtained.

Another limitation of current methods of working with embryonic stem cells is the necessity of culturing the cells in the presence of a feeder layer of cells. In particular, human embryonic stem cells are often cultured with a feeder layer including mouse cells. This can result in uptake of mouse proteins or other molecules by the stem cells, with negative implications for use of the stem cells in medical procedures, research or drug screening.

Thus, methods, compositions and systems for producing and maintaining a substantially homogeneous population of undifferentiated embryonic stem cells, and particularly human embryonic stem cells, are needed.

In addition to a continuing need for methods, compositions and systems for producing and maintaining a substantially homogeneous population of undifferentiated embryonic stem cells, methods, compositions and systems for producing and maintaining a substantially homogeneous population of a desired differentiated cell type, particularly human differentiated cells, are necessary.

SUMMARY OF THE INVENTION

A method for obtaining a substantially homogeneous population of undifferentiated embryonic stem cells is provided which includes incubating a population of embryonic stem cells with an amount of a selection agent, the selection agent effective to reduce or eliminate differentiated embryonic stem cells from the population of cells such that a substantially homogeneous population of undifferentiated embryonic stem cells is obtained. The embryonic stem cells may be embryonic stem cells from any species. In a preferred embodiment, the embryonic stem cells are human embryonic stem cells.

A method according to embodiments of the present invention is provided for obtaining a substantially homogeneous population of undifferentiated embryonic stem cells. Such a method includes incubating a population of embryonic stem cells with an amount of ceramide effective to induce apoptosis in differentiated embryonic stem cells, such that a substantially homogeneous population of undifferentiated embryonic stem cells resistant to ceramide-induced apoptosis is obtained. The embryonic stem cells may be embryonic stem cells from any species. In a preferred embodiment, the embryonic stem cells are human embryonic stem cells.

In particular embodiments of methods of the present invention, no feeder cells are used. Thus, a substantially homogeneous population of undifferentiated embryonic stem cells is obtained without exposing the cells to feeder cells, avoiding contamination of the substantially homogeneous population of undifferentiated embryonic stem cells.

Also provided by embodiments of methods of the present invention are methods for obtaining a substantially homogeneous population of differentiated cells. Such a method includes incubating a population of embryonic stem cells with an amount of ceramide effective to induce apoptosis in differentiated embryonic stem cells, such that a substantially homogeneous population of undifferentiated embryonic stem cells resistant to ceramide-induced apoptosis is obtained. The substantially homogeneous population of undifferentiated embryonic stem cells is then treated so as to differentiate the embryonic stem cells, resulting in a substantially homogeneous population of differentiated cells.

Methods of maintaining a population of undifferentiated embryonic stem cells are additionally disclosed according to embodiments of the present invention. Such methods include culturing a substantially homogeneous population of undifferentiated embryonic stem cells in the presence of a selection agent effective to induce apoptosis in differentiated embryonic stem cells, thereby maintaining the population of substantially homogeneous undifferentiated embryonic stem cells in an undifferentiated state. In particular embodiments of inventive methods of maintaining a population of undifferentiated embryonic stem cells, no feeder cells are used in culturing the substantially homogeneous population of undifferentiated embryonic stem cells.

A kit for producing and/or maintaining a substantially homogeneous population of undifferentiated embryonic stem cells, preferably in the absence of feeder cells, is detailed herein according to embodiments of the present invention. An inventive kit includes a culture medium for embryonic stem cells and a selection agent in particular embodiments. The culture medium and selection agent may be provided in separate containers, along with instructions for mixing. Alternatively, the culture medium and selection agent are provided in combination. Instructions for use of the medium and selection agent are optionally provided. A selection agent included in a kit according to embodiments of the present invention is preferably an apoptosis-inducing agent. Also preferably, the apoptosis-inducing agent includes ceramide.

A kit provided according to the present invention optionally also includes a population of embryonic stem cells. The provided population of embryonic stem cells is a population of human embryonic stem cells in preferred embodiments.

In additional embodiments of a kit according to the present invention, a reagent inducing the substantially homogeneous population of undifferentiated embryonic stem cells to differentiate is included. Such a reagent may be included in a separate container and later mixed with medium or may be included in combination with the medium. A specialized culture medium for maintaining a population of differentiated cells is also optionally provided.

A method for obtaining a substantially homogeneous population of embryonic stem cells is disclosed according to embodiments of the present invention which includes providing a population of embryonic stem cells heterogeneous for a marker of differentiation and incubating the population of cells with an amount of a selection agent effective to select a portion of the population of cells, such that a desired population of selected cells is obtained.

A method for obtaining a substantially homogeneous population of embryonic stem cells according to an embodiment of the present invention is described herein which includes providing a population of embryonic stem cells heterogeneous for sensitivity to ceramide-induced apoptosis and incubating the population of cells with an amount of ceramide effective to induce apoptosis in a portion of the population of cells, such that a substantially homogeneous population of embryonic stem cells resistant to ceramide-induced apoptosis is obtained.

A method for obtaining a desired population of differentiated cells is detailed according to embodiments of the present invention which includes providing a population of embryonic stem cells heterogeneous for sensitivity to ceramide-induced apoptosis and incubating the population of cells with an amount of ceramide effective to induce apoptosis in a portion of the population of cells, resulting in a population of embryonic stem cells substantially homogeneous for resistance to ceramide-induced apoptosis. The substantially homogeneous population of embryonic stem cells is treated to differentiate the embryonic stem cells, such that a desired population of differentiated cells is obtained.

A method of producing and/or maintaining a desired population of cells is provided according to embodiments of the present invention which includes providing a population of embryonic stem cells heterogeneous for a characterized response to a first selection agent and incubating the population of cells with a first amount of the first selection agent effective to select a sub-population of cells having a characterized response to the first selection agent, such that a population of embryonic stem cells substantially homogeneous for a characterized response to first selection agent is obtained. The substantially homogeneous population of embryonic stem cells is then cultured in the presence of a second amount of a second selection agent effective to select a second population of cells, with the proviso that no feeder cells are used in culturing, thereby producing and maintaining a desired population of cells.

A method of producing and/or maintaining a substantially homogeneous population of embryonic stem cells derived from a first species uncontaminated by material derived from feeder cells of the same or different species is provided which includes providing a population of embryonic stem cells derived from a first species, wherein the population of embryonic stem cells is heterogeneous for sensitivity to a first apoptosis-inducing agent. The embryonic stem cells are incubated with a first amount of the first apoptosis-inducing agent effective to induce apoptosis in differentiated embryonic stem cells sensitive to the first apoptosis-inducing agent, such that a population of substantially homogeneous embryonic stem cells is obtained. The population of substantially homogeneous embryonic stem cells is then cultured in the presence of a second amount of a second apoptosis-inducing agent effective to induce apoptosis in differentiated cells sensitive to the second apoptosis-inducing agent. In one such embodiment, neither the population of embryonic stem cells derived from a first species nor the population of substantially homogeneous embryonic stem cells is exposed to feeder cells prior to or during culturing. Thus, a substantially homogeneous population of embryonic stem cells derived from a first species is produced and maintained without contamination by material derived from feeder cells. The embryonic stem cells may be derived from any species. In a preferred embodiment, the embryonic stem cells are human embryonic stem cells.

A method of producing a substantially homogeneous population of embryonic stem cells derived from a first species uncontaminated by feeder cells, the feeder cells derived from a second species, is provided which includes providing a population of embryonic stem cells derived from a first species, the population of embryonic stem cells heterogeneous for sensitivity to a first apoptosis-inducing agent. The population of embryonic stem cells is incubated with a first amount of the first apoptosis-inducing agent effective to induce apoptosis in a sub-population of the population of embryonic stem cells, the sub-population sensitive to the first apoptosis-inducing agent, such that a population of substantially homogeneous embryonic stem cells is obtained, with the proviso that neither the population of embryonic stem cells derived from a first species nor the population of substantially homogeneous embryonic stem cells is exposed to feeder cells derived from a second species prior to or during culturing, thereby producing a substantially homogeneous population of embryonic stem cells derived from a first species uncontaminated by feeder cells derived from a second species.

A composition for producing a desired cell population is provided which includes a selection agent. In particular embodiments, the selection agent is associated with a nanoparticle.

DETAILED DESCRIPTION OF THE PREFERRED EMBODIMENTS

Compositions, methods and systems are provided according to the present invention for specifically reducing or eliminating differentiating and/or differentiated embryonic stem cells. Such compositions, methods and systems are useful in producing and/or maintaining substantially homogeneous undifferentiated stem cell populations for uses illustratively including research, screening or medical procedures. Substantially homogeneous undifferentiated stem cell populations produced and/or maintained using compositions, methods and systems according to the present invention are advantageously used in differentiation methods to produce a substantially homogeneous population of a desired type of differentiated cells which have numerous used illustratively including research, screening, or medical procedures.

Additionally, compositions, methods and systems are provided according to the present invention for culturing and maintaining undifferentiated embryonic stem cells in the absence of a feeder layer such that the undifferentiated cells are maintained in an undifferentiated state.

A method for obtaining a substantially homogeneous population of undifferentiated embryonic stem cells is provided which includes incubating a population of embryonic stem cells with an amount of a selection agent, the selection agent effective to reduce or eliminate differentiated embryonic stem cells from the population of cells such that a substantially homogeneous population of undifferentiated embryonic stem cells is obtained.

In one embodiment of a method according to the present invention, the selection agent is a survival agent effective to promote survival of a portion of the population of cells. Alternatively, the selection agent is a differentiation agent effective to promote differentiation of a portion of the population of cells, such that a desired population of selected differentiated cells is obtained.

A selection agent is an apoptosis-inducing agent in a preferred embodiment of a method according to the present invention. It is a finding of the present invention that sensitivity to induction of apoptosis is a marker of differentiation and, conversely, that resistance to selection agent induced apoptosis is characteristic of undifferentiated cells. Thus, according to methods of the present invention, an apoptosis-inducing agent is effective to induce apoptosis in differentiated embryonic stem cells and does not induce apoptosis in undifferentiated embryonic stem cells. Thus, the apoptosis-inducing agent is effective to select for a population of undifferentiated cells resistant to induction of apoptosis by the apoptosis-inducing agent.

The term "embryonic stem cell" as used herein refers to cells characterized by the ability to self-replicate and characterized by being pluripotent. A pluripotent cell is one capable of differentiating into a cell of any of the three primary germinal layers, endoderm, mesoderm and ectoderm. Pluripotency of embryonic cells is confirmed by established assays such as formation of teratomas containing endoderm, mesoderm and ectoderm cells following introduction of the putative pluripotent embryonic stem cells into severe combined immunodeficient (SCID) mice. Details of such assays are found in standard references, such as Thomson et al., Biol. Reprod., 55:254, 1996.

An embryonic stem cell is derived from an embryo at any stage after fertilization. Particularly preferred are human embryonic stem cells derived from a preimplantation or peri-implantation embryo, especially from the inner cell mass of a blastocyst stage embryo. Embryonic stem cells used in methods according to the present invention include primary cultures derived directly from an embryo. In addition, embryonic stem cells used in methods according to the present invention include established cell lines of embryonic stem cells.

Briefly described, hES cells are obtained from human blastocysts, obtained by in vivo fertilization or in vitro fertilization.

Blastocysts are exposed briefly to a protease, such as pronase, to remove the zona pellucida. Inner cell masses are excised and plated in hES cell media as described herein. Alternatively, hES cell line cells are obtained from a commercial or repository source.

Embryonic stem cells are also obtained by somatic cell nuclear transfer, for instance as described in Gurdon J B, et al., Proc Natl Acad Sci USA., 2003, 100 Suppl 1:11819-22. or from embryos derived by parthenogenesis as described in Vrana K E, et al., Proc Natl Acad Sci USA., 2003, 100 Suppl 1:11911-6, Erratum in: Proc Natl Acad Sci USA. Jan. 13, 2004; 101(2):693; and Cibelli J B et al., Science. 2002, 295 (5556):819.

Human embryonic stem cells and their characteristics as well as general techniques and reagents used to isolate, culture, maintain and/or differentiate embryonic stem cells are described herein and in standard references including Thomson et al., Science 282:1145-1147, 1998; K. Turksen Ed.), Embryonic Stem Cell Protocols: Differentiation Models, Methods in Molecular Biology, Humana Press, 2006; K. Turksen (Ed.), Embryonic Stem Cell Protocols: Isolation And Characterization, Methods in Molecular Biology, Humana Press, 2006; and A. Y. Chiu and M. S. Rao ads.) Human Embryonic Stem Cells, AACC Press, 2003. Human embryonic stem cells obtained by any method may be used in methods according to the present invention.

Although methods and compositions according to embodiments of the present invention are described herein primarily with reference to primate, and specifically human embryonic stem cells, it is appreciated that inventive methods and compositions are useful in conjunction with embryonic stem cells from non-human species. For example, methods and compositions according to embodiments of the present invention are useful in conjunction with any vertebrate embryonic stem cells illustratively including domestic animals such as dogs and cats; livestock such as cattle, horses, pigs, and goats; research animals such as rats, mice, guinea pigs and rabbits; pluripotent rhesus monkey embryonic stem cells described in Thomson et al., Proc. Natl. Acad. Sci. USA, 92:7844, 1995; pluripotent marmoset embryonic stem cells described in Thomson et al., Biol. Reprod., 55:254-259, 1996; and mouse, chicken and others reviewed in Prelle, K, et al., Cells Tissues Organs., 165:220-36, 1999.

The terms "feeder cells" and "feeder layer" are used herein to refer to cells of one type which are co-cultured with cells of a second type in order to provide a supportive environment for growth and/or maintenance of the cells of the second type.

The term "undifferentiated" as used herein refers to pluripotent embryonic stem cells which have not developed a characteristic of a more specialized cell. As will be recognized by one of skill in the art, the terms "undifferentiated" and "differentiated" are relative with respect to each other. An embryonic cell which is "differentiated" has a characteristic of a more specialized cell. Differentiated and undifferentiated cells are distinguished from each other by several well-established criteria, including morphological characteristics such as relative size and shape, ratio of nuclear volume to cytoplasmic volume; and expression characteristics such as detectable presence of known markers of differentiation. A marker of differentiation indicating that cells are differentiated or undifferentiated includes a protein, carbohydrate, lipid, nucleic acid, functional characteristic and/or morphological characteristic which is specific to a differentiated cell.

Table 1 lists exemplary markers of differentiated and undifferentiated cells.

TABLE 1

| Marker Name | Cell Type |
| --- | --- |
| Fetal liver kinase-1 | Endothelial |
| Smooth muscle cell-specific myosin heavy chain | Smooth muscle |
| Vascular endothelial cell cadherin | Smooth muscle |
| Bone-specific alkaline phosphatase | Osteoblast |
| Hydroxyapatite | Osteoblast |
| Osteocalcin | Osteoblast |
| Bone morphogenetic protein receptor | Mesenchymal stem and progenitor cells |
| CD4 and CD8 | White blood cell (WBC) |
| CD34 | Hematopoietic stem cell (HSC), satellite, endothelial progenitor |
| CD34$^+$Sca1$^+$Lin$^-$ profile | Mesenchymal stem cell (MSC) |
| CD38 | Absent on HSC Present on WBC lineages |
| CD44 | Mesenchymal |
| c-Kit | HSC, MSC |
| Colony-forming unit (CFU) | HSC, MSC progenitor |
| Fibroblast colony-forming unit (CFU-F) | Bone marrow fibroblast |
| Hoechst dye | Absent on HSC |
| Leukocyte common antigen (CD45) | WBC |
| Lineage surface antigen (Lin) | HSC, MSC Differentiated RBC and WBC lineages |
| Mac-1 | WBC |
| Muc-18 (CD146) | Bone marrow fibroblasts, endothelial |
| Stem cell antigen (Sca-1) | HSC, MSC |
| Stro-1 antigen | Stromal (mesenchymal) precursor cells. hematopoietic cells |
| Thy-1 | HSC, MSC |
| Collagen types II and IV | Chondrocyte |
| Keratin | Keratinocyte |
| Sulfated proteoglycan | Chondrocyte |
| Fatty acid transporter (FAT) | Adipocyte |
| Adipocyte lipid-binding protein (ALBP) | Adipocyte |
| Y chromosome | Male cells |
| Karyotype | Most cell types |
| Albumin | Hepatocyte |
| B-1 integrin | Hepatocyte |
| CD133 | Neural stem cell, HSC |
| Glial fibrillary acidic protein (GFAP) | Astrocyte |
| Microtubule-associated protein-2 | Neuron |
| Myelin basic protein (MPB) | Oligodendrocyte |
| Nestin | Neural progenitor |
| Neural tubulin | Neuron |
| Neurofilament (NF) | Neuron |
| Neurosphere | Embryoid body (EB), ES |

TABLE 1-continued

| Marker Name | Cell Type |
| --- | --- |
| Noggin | Neuron |
| O4 | Oligodendrocyte |
| O1 | Oligodendrocyte |
| Synaptophysin | Neuron |
| Tau | Neuron |
| Cytokeratin 19 (CK19) | Pancreatic epithelium |
| Glucagon | Pancreatic islet |
| Insulin | Pancreatic islet |
| Insulin-promoting factor-1 (PDX-1) | Pancreatic islet |
| Nestin | Pancreatic progenitor |
| Pancreatic polypeptide | Pancreatic islet |
| Somatostatin | Pancreatic islet |
| Alkaline phosphatase | Embryonic stem (ES), embryonal carcinoma (EC) |
| Alpha-fetoprotein (AFP) | Endoderm |
| Bone morphogenetic protein-4 | Mesoderm |
| Brachyury | Mesoderm |
| Cluster designation 30 (CD30) | ES, EC |
| Cripto (TDGF-1) | ES, cardiomyocyte |
| GATA-4 gene | Endoderm |
| GCTM-2 | ES, EC |
| Genesis (transcription factor) | ES, EC |
| Germ cell nuclear factor (transcription factor) | ES, EC |
| Hepatocyte nuclear factor-4 (HNF-4) | Endoderm |
| Nestin | Ectoderm, neural and pancreatic progenitor |
| Neuronal cell-adhesion molecule | Ectoderm |
| Oct-4 | ES, EC |
| Pax6 | Ectoderm |
| Stage-specific embryonic antigen-3 (SSEA-3) | ES, EC |
| Stage-specific embryonic antigen-4 (SSEA-4) | ES, EC |
| Stem cell factor (SCF or c-Kit ligand) | ES, EC, HSC, MSC |
| Telomerase | ES, EC |
| TRA-1-60 | ES, EC |
| TRA-1-81 | ES, EC |
| Vimentin | Ectoderm, neural and pancreatic progenitor |
| MyoD and Pax7 | Myoblast, myocyte |
| Myogenin and MR4 | Skeletal myocyte |
| Myosin heavy chain | Cardiomyocyte |
| Myosin light chain | Skeletal myocyte |

Further markers useful in distinguishing undifferentiated and differentiated embryonic stem cells are listed in Tables 2 and 3.

Table 2 lists markers of undifferentiated cells and markers of early stages of differentiation.

TABLE 2

| Target Name | Description |
| --- | --- |
| | Undifferentiated Cell Markers |
| Oct-4* | A member of POU transcription factors - stem cell pluripotency marker. |
| Nanog* | DNA binding transcription factor - stem cells pluripotency marker. |
| Nucleostemin | Found in the nucleoli of embryonic and adult CNS stem cells, but not in differentiated cells. |
| | Signaling Pathway Related |
| PAR-4 | PKC-zeta inhibitor, ceramide induces apoptosis if PAR-4 is co-localized with Oct-4 in mouse ESCs. |
| | Cell Cycle Related |
| Chk2 | Cell-cycle protein, located on centrosomes causing lack of G-1 checkpoint in ESCs. |

TABLE 2-continued

| Target Name | Description |
|---|---|
| | Ceramide Metabolism Related |
| Ceramidase | Converts ceramide into less toxic sphingosine. |
| Sphingomyelin Synthase | Converts ceramide into less toxic sphingomyelins. |
| Glucosyl Ceramide Synthase | Converts ceramide into less toxic glucosylceramide. |
| | Early Differentiation Markers |
| Pax6* | A highly conserved transcription factor - early differentiation marker. |
| Nestin* | Intermediate filament protein, mainly found in neuroprogenitor cells, also detected in haematopoietic and pancreatic islet progenitors. |
| Musashi-1* | RNA-binding protein specifically expressed in neuroprogenitor cells. |
| Brachyury* | T-box family of transcription factors - used as the earliest indicator of mesoderm formation. |
| Vimentin* | Intermediate filament protein - used as a marker for primitive neuroectoderm. |
| α-Fetoprotein* | Protein expressed during development of primitive endoderm. |
| GATA-4* | GATA family transcription factor - widely expressed during endodermal differentiation. |

Table 3 lists markers of neuronal and glial differentiation.

TABLE 3

| Gene Name | Description | Assay ID # |
|---|---|---|
| Neuroprogenitor Markers | | |
| Nestin* | Mainly found in neuroprogenitor cells, also detected in haematopoietic and pancreatic islet progenitors. | Hs00707120_s1 |
| Neurogenin-2 (Ngn-2) | Proneuronal protein - expressed in neuroprogenitor cells. | Hs00702774_s1 |
| Musashi-1* | RNA-binding protein - specifically expressed in neuroprogenitor cells. | Hs00159291_m1 |
| Mature Neuron Markers | | |
| Microtubule Associated Protein-2 (MAP-2)* | Dendrite-specific protein - expressed specifically in the dendritic branching of neurons. | Hs00159041_m1 |
| Neurofilament-3 (NF-3)* | Structural protein - specifically found in differentiated neurons. | Hs00193572_m1 |
| Synaptophysin (SYP)* | Integral membrane protein - associated with synaptic vesicles of mature neurons. | Hs00300531_m1 |
| Tyrosine Hydroxylase (TH) | Key regulatory enzyme in dopamine biosynthesis | Hs00165941_m1 |
| Tryptophan Hydroxylase 2 (TPH2) | Key regulatory enzyme in serotonin biosynthesis | Hs00542783_m1 |
| Neuroglial Markers | | |
| Myelin Basic Protein (MBP)* | Mature oligodendrocyte specific protein. | Hs00175245_m1 |
| Glial Fibrillary Acidic Protein (GFAP)* | Intermediate filament protein - marker for mature astrocytes. | Hs00157674_m1 |

In one embodiment, "substantially homogeneous" describes a population of cells in which more than 50% of the cells are undifferentiated. In a further embodiment, a substantially homogeneous population of cells is one in which more than 70% of the cells are undifferentiated. In another embodiment, a substantially homogeneous population of cells is one in which more than 80% of the cells are undifferentiated. In another embodiment, a substantially homogeneous population of cells is one in which more than 90% of the cells are undifferentiated. In a further embodiment a substantially homogeneous population of cells is one in which more than 95% of the cells are undifferentiated. In another embodiment, a substantially homogeneous population of cells is one in which more than 99% of the cells are undifferentiated.

A population of cells is assayed for one or more markers of differentiation to determine whether the population of cells is substantially homogeneous.

The production and/or maintenance of a substantially homogeneous population of ESCs and/or a differentiated cell type may be measured by assessing the proportion of undifferentiated embryonic stem cells and/or differentiated embryonic stem cells for particular markers of undifferentiated cells and/or differentiated cells. For instance, relative ratios of transcription products for markers of undifferentiated cells such as Oct4, neuroprogenitor markers such as nestin and Ngn-2, and markers of mature neuron markers such as β-tubulin and TPH2 is assessed by quantitative RT-PCR. Also, production and localization of markers of undifferentiated cells, as well as neuroprogenitor and mature neuron markers is assessed by immunocytochemistry.

Markers of undifferentiated embryonic stem cells and differentiated cells are assayed by any of various methods such as antibody-based detection techniques using an antibody specific for a particular marker. Antibody-based techniques include immunofluorescence and immunoblotting. Further assays include assays for detection of mRNAs encoding a particular marker. Such assays include polymerase chain reaction, blot hybridization (also known as Northern blots) and in situ hybridization. Details of these and other such assays are described herein and in standard references including J. Sambrook and D. W. Russell, Molecular Cloning: A Laboratory Manual, Cold Spring Harbor Laboratory Press; 3rd ed., 2001; F. M. Ausubel, Ed., Short Protocols in Molecular Biology, Current Protocols; 5th ed., 2002; and E. Harlow and D. Lane, Antibodies: A Laboratory Manual, Cold Spring Harbor Laboratory Press, 1988.

In the context of methods and compositions according to embodiments of the present invention, it is found that differentiated cells and undifferentiated pluripotent embryonic stem cells are distinguished by sensitivity of differentiated cells to induction of apoptosis using a selection agent. In comparison, relatively undifferentiated embryonic stem cells are not sensitive to a selection agent included in methods and compositions according to embodiments of the present invention and are therefore not induced to undergo apoptosis when incubated with such a selection agent. In one embodiment, and surprisingly, a population of embryonic stem cells sensitive to induction of apoptosis by a selection agent in methods according to the present invention is characterized by presence of one or more markers of undifferentiated embryonic stem cells and by one or more markers of differentiated cells. These cells are referred to as "differentiated" herein and are eliminated or reduced by treatment of a population of embryonic stem cells with a selection agent.

An apoptosis-inducing agent used in embodiments of methods according to the present invention is a biologically active lipid second messenger or a biologically active analog of a lipid second messenger. Combinations of one or more biologically active lipid second messengers and biologically active analogs of a lipid second messenger are optionally used in particular embodiments.

The terms "biologically active lipid second messenger" and "biologically active analog of a lipid second messenger" as used herein refer to lipid second messengers, derivatives and analogs characterized by particular biological activity, specifically, the ability to inhibit growth and/or induce apoptosis in cells. For example, biologically active lipid second messengers, derivatives and analogs inhibit cell proliferation and induce apoptosis in cells such as HT-29 and HCT-116 human colon cancer cells as described in Eun, H. A. And Schroeder, J. J., Exp. Biol. Medicine, 2002, 227: 345-353. Further, biologically active lipid second messengers, derivatives and analogs inhibit proliferation of glomerular mesangial cells as described in Mandal, A. et al., J. Biol. Chem., 272:20306-20311, 1997. Assays for growth inhibition and induction of apoptosis are known, and examples of such assays are described herein.

The term "derivative" refers to a chemically modified lipid-derived second messenger having biological activity effective to inhibit proliferation of cells and/or induce apoptosis in cells. Chemical modification illustratively includes replacement of a hydrogen with a substituted or unsubstituted, straight chain or branched, saturated or unsaturated alkyl; hydroxyl; amino; alkoxy; carboxyl; or nitro group. A preferred group of derivatives include those having increased resistance to degradation, exemplified by methylcarbamyl ceramide.

The term "analog" refers to a molecule which is structurally similar to a lipid-derived second messenger and has biological activity effective to inhibit proliferation of cells and/or induce apoptosis in cells.

An apoptosis-inducing agent which is a biologically active lipid second messenger is a biologically active ceramide in embodiments of methods according to the present invention. A biologically active analog of a lipid second messenger illustratively includes a biologically active ceramide derivative or analog.

Biologically active lipid second messengers are obtained by techniques including isolation from natural sources, such as cells or eggs, by synthetic techniques including chemical synthesis and enzymatic modification of isolated lipids. Suitable techniques are described, for instance, in F. D. Gunstone, Lipid Synthesis and Manufacture, Chemistry and Technology of Oils and Fats, Blackwell, 1998. Biologically active lipid second messengers are commercially available in purified form for use in methods according to the present invention.

Additionally, apoptosis-inducing agent includes an agent effective to increase ceramide in an embryonic stem cell.

The term "ceramide" refers to a biologically active ceramide, ceramide derivative or ceramide analog having a pro-apoptotic effect on differentiated hESCs. Ceramides generally include a sphingoid base linked to a fatty acid via an amide bond. The term "ceramide" as used herein refers to any N-acylsphingosine including sphingolipids in which the sphingosine is acylated with a fatty acid acyl CoA derivative to form an N-acylsphingosine. Ceramides may be isolated from natural sources or chemically synthesized. Examples include N-Acetoyl-D-erythro-Sphingosine (C2 Ceramide); N-Butyroyl-D-erythro-Sphingosine (C4 Ceramide); N-Hexanoyl-D-erythro-Sphingosine (C6 Ceramide); N-Octanoyl-D-erythro-Sphingosine (C8 Ceramide); N-Decanoyl-D-erythro-Sphingosine (C10 Ceramide); N-Lauroyl-D-erythro-Sphingosine (C12 Ceramide); N-Myristoyl-D-erythro-Sphingosine (C14 Ceramide); N-Palmitoyl-D-erythro-Sphingosine (C16 Ceramide); N-Heptadecanoyl-D-erythro-Sphingosine (C17 Ceramide); N-Stearoyl-D-erythro-Sphingosine (C18 Ceramide); N-Oleoyl-D-erythro-Sphingosine (C18:1 Ceramide); and N-Arachidoyl-D-erythro-Sphingosine (C20 Ceramide). A biologically active ceramide is characterized by a 4,5-double bond. For example, in contrast to a biologically active ceramide, a biologically inactive ceramide, dihydro ceramide, e.g. an N-acylsphinganine such as N-hexanoyl-D-erythro sphinganine, is saturated at the 4, 5 site. Ceramides and lipid second messengers are known in the art as exemplified in Hannun, Y. A et al., Ceramide: A novel Second Messenger and Lipid Mediator, in Bell, R. M. et al., Lipid Second Messengers, Handbook of Lipid Research, Springer, 1996.

Broadly, in one embodiment, ceramide has the chemical formula $CH_3(CH_2)_{12}CH=CH-CHOH-CH(CH_2OH)-NH-CO-R$, where R is a C1-C20 alkyl group, preferably a straight chain alkyl group. Optionally, R may be a C1, C2, C3, C4, C5, C6, C7, C8, C9, C10, C11, C12, C13, C14, C15, C16, C17, C18, C19 or C20 alkyl, alkenyl or alkynyl group, substituted or unsubstituted, straight chain or branched.

In a particularly preferred embodiment, the apoptosis-inducing agent is C6 ceramide.

Optionally, ceramide derivatives or analogs include sphingomyelins, such as those having the chemical formula $CH_3(CH_2)_{12}CH=CH-CHOH-CH(CH_2PO_4CH_2CH_2-N(CH_3)_3)-NH-CO-R$, where R is a C1-C20 alkyl group, preferably a straight chain alkyl group. Optionally, R may be a C1-C20 alkyl, alkenyl or alkynyl group, substituted or unsubstituted, straight chain or branched.

Optionally, the selection agent includes a compound selected from the group consisting of: a dimethyl sphingosine, a trimethyl sphingosine, an ether-linked diglyceride, an ether-linked phosphatidic acid, a sphingosine a sphinganine. Combinations of these compounds and other selection agents are also contemplated.

A selection agent further illustratively includes a dimethyl sphingosine, a trimethyl sphingosine, an ether-linked diglyceride, an ether-linked phosphatidic acid, a sphingosine or a sphinganine. Combinations of such selection agents are optionally used in particular embodiments.

Lipid-derived second messengers illustratively include phosphatidic acid, lyso-phosphatidic acid, alkyl-phosphatidic acid, allyl-lyso-phosphatidic acid, ether-linked diglyceride and ether-linked diacylglyceride. Combinations of such lipid derived second messengers are optionally used in particular embodiments.

Optionally, ceramide or a derivative or analog of ceramide is modified to produce a ceramide derivative which inhibits conversion of the ceramide derivative to glycosylceramide, sphingomyelins or sphingosines. Such inhibition prevents or lessens the shunting of the pro-apoptotic ceramide derivative into less toxic forms, thereby promoting apoptosis.

Ceramide synthesis and metabolic pathways may be involved in mechanisms disposing cells to apoptosis. Increased de novo ceramide synthesis from serine and palmitoyl-CoA or degradation of sphingomyelins causes cytotoxicity. Conversion of ceramide to glycosylceramide, sphingomyelins or sphingosines shunts ceramide into less toxic forms. In this latter case, phosphorylation of sphingosine, derived from ceramide, stimulates anti-apoptotic metabolic pathways and acts to oppose cytotoxic actions of ceramide. Note that SSEA-3 and SSEA-4, the most commonly used undifferentiated hESC markers, are glycosphingolipids that originate from ceramide. Immunofluorescence using antibodies specific for these markers demonstrates their presence in both embryonic stem cells sensitive to ceramide induced apoptosis, such as those found at the periphery of human ES cell colonies cultured in the presence of mouse feeder cells, and those resistant to ceramide apoptosis, found in more central locations in such colonies.

A population of embryonic stem cells may contain both undifferentiated embryonic stem cells and differentiated embryonic stem cells and therefore be heterogeneous for a marker of differentiation. For example, a population of embryonic stem cells may include differentiated embryonic stem cells which are sensitive to ceramide-induced apoptosis, that is, incubation of differentiated embryonic stem cells which are sensitive to ceramide-induced apoptosis with an effective amount of ceramide induces apoptosis in the sensitive cells. In contrast, undifferentiated embryonic stem cells are not sensitive to ceramide and incubation of undifferentiated embryonic stem cells with amounts of ceramide effective to induce apoptosis in differentiated embryonic stem cells do not induce apoptosis in undifferentiated embryonic stem cells.

Several characteristics of ceramide sensitive embryonic stem cells are characterized herein. In cultures including feeder cells, ceramide sensitive embryonic stem cells have been in contact with the surrounding mouse feeder cells—a condition known to promote contact-induced intracellular changes. Further, ceramide-sensitive hESCs appear to have higher cytoplasmic to nuclear ratio, indicative of differentiating cells. In addition, ceramide-sensitive cells are located towards the edges of ESC colonies in these co-cultures.

In addition to differential sensitivity to ceramide-induced apoptosis, differentiated embryonic stem cells and undifferentiated embryonic stem cells differ in expression of particular markers of differentiation, such as a protein or mRNA characteristic of a progenitor cell or expression of a protein or mRNA characteristic of a precursor cell.

Differentiated embryonic stem cells to be eliminated from a heterogeneous population of embryonic stem cells may also have a detectable presence of a molecular marker of differentiation, such as a protein or nucleic acid typically present in a differentiating and/or differentiated cell. Ceramide-sensitive cells may also show differences in presence and location of suspected proapoptotic factors, including PAR-4, Chk-2, and ceramide-converting enzymes. In particular, early progenitor cell markers of ectodermal lineage such as nestin, mesodermal lineage such as brachyury, and/or endodermal lineage such as alpha fetoprotein are markers of differentiated cells. These and other such factors may be assayed to detect a marker of differentiation associated with sensitivity to ceramide-induced apoptosis.

A hallmark of pluripotent embryonic stem cells is the expression of Stage-Specific Embryonic Antigens (SSEA-3 and SSEA-4) that are actually products of de novo ceramide metabolism. These globo-series glycolipids are first identified as a hallmark of human embryonic carcinoma cells (Wenk J, et al., Int J Cancer, 1994 58:108-115) and have become a common marker to characterize human embryonic stem cells (Thomson J A, et al., Science. 1998, 282:1145-1147). Spiegel and Milstien (J Biol Chem., 2002, 277:25851-4) stated that there is a fine balance between ceramide (pro-apoptotic and anti-proliferative), and its metabolite, sphingosine-1-phosphate (S1P), which exerts opposite effects. In fact, biochemical regulation of ceramidase serves as a critical control point regulating the dynamic flux between these metabolites. In addition, endogenous ceramide levels can be reduced by activation of glucosylceramide synthase, or sphingomyelin synthase (Spiegel and Milstien, 2000). Thus, in one embodiment, a population of ESCs heterogeneous for a marker of differentiation includes a subpopulation of differentiated cells at the periphery of an ESC colony having lower levels and/or activity of one or more enzymes which ordinarily convert ceramide to a less toxic form and a second subpopulation of undifferentiated cells having higher levels and/or activity of such enzymes. Such enzymes include glucosyl ceramide synthase, ceramidase and sphingomyelin synthase. Thus, in one embodiment a selection agent is an agent effective to increase ceramide in an embryonic stem cell.

In addition, ceramide induces apoptosis specifically in dividing cells, but not in resting cells. Elevation of ceramide prior to the G0/G1 junction primes cells for ceramide-induced apoptosis during the G1-to-S phase transition, unless ceramide is converted to glycosphingolipids. Ceramide-dependent upregulation of p21/p27 and Bax/Bad induces G1 arrest and apoptosis, respectively. On the other hand, conversion of ceramide to glycosphingolipids promotes upregulation of Bcl-2 and downregulation of Bax/Bad resulting in cell differentiation and proliferation. Unlike other proliferating cells, undifferentiated embryonic stem cells lack the G1 checkpoint during the G1-to-S phase transition. The lack of a G1 checkpoint is due to centrosomal localization of checkpoint kinase 2 (chk2) instead of its presence in the nucleus (Hong Y, and Stambrook P J. Proc Natl Acad Sci USA., 2004, 101:14443-8). The absence of a G1 checkpoint may uniquely protect hES cells from ceramide-induced apoptosis. Thus, in one embodiment, a population of ESCs heterogeneous for a marker of differentiation includes a differentiated subpopulation of cells having chk2 in the nucleus and an undifferentiated subpopulation of cells having chk2 at the centrosome.

A method according to embodiments of the present invention is provided for obtaining a substantially homogeneous population of undifferentiated embryonic stem cells. Such a method includes incubating a population of embryonic stem cells with an amount of ceramide effective to induce apoptosis in differentiated embryonic stem cells, such that a substantially homogeneous population of undifferentiated embryonic stem cells resistant to ceramide-induced apoptosis is obtained. The embryonic stem cells may be embryonic stem cells from any species. In a preferred embodiment, the embryonic stem cells are human embryonic stem cells.

An amount of an apoptosis-inducing agent effective to induce apoptosis in differentiated embryonic stem cells is also an amount which has no apoptosis-inducing effect in undifferentiated embryonic stem cells. An effective amount of an apoptosis-inducing agent effective to induce apoptosis in differentiated embryonic stem cells is also an amount which has no apoptosis-inducing effect in undifferentiated embryonic stem cells and is in the range of about 1 nanomolar-50 millimolar, inclusive.

An amount of ceramide effective to induce apoptosis in differentiated embryonic stem cells is also an amount which has no apoptosis-inducing effect in undifferentiated embryonic stem cells, less than about 30 micromolar. Low doses of ceramide, less than 30 micromolar, result in selection of a highly homogeneous population of undifferentiated human ES cells that are positive for stem cell markers and resistant to ceramide-induced apoptosis.

An effective amount of ceramide effective to induce apoptosis in differentiated embryonic stem cells is also an amount which has no apoptosis-inducing effect in undifferentiated embryonic stem cells and is in the range of about 0.1-25 micromolar, inclusive. In further embodiments, an effective amount of ceramide effective to induce apoptosis in differentiated embryonic stem cells is also an amount which has no apoptosis-inducing effect in undifferentiated embryonic stem cells is in the range of about 0.5-20 micromolar, inclusive. In still further embodiments, an effective amount of ceramide effective to induce apoptosis in differentiated embryonic stem cells is also an amount which has no apoptosis-inducing effect in undifferentiated embryonic stem cells is in the range of about 1-15 micromolar, inclusive, and further preferably in the range of about 3-10 micromolar, inclusive.

In particular embodiments of methods of the present invention, no feeder cells are used. Thus, a substantially homogeneous population of undifferentiated embryonic stem cells is obtained without exposing the cells to feeder cells, avoiding contamination of the substantially homogeneous population of undifferentiated embryonic stem cells.

Methods of maintaining a population of undifferentiated embryonic stem cells are additionally disclosed according to embodiments of the present invention. Such methods include culturing a substantially homogeneous population of undifferentiated embryonic stem cells in the presence of a selection agent effective to select for undifferentiated cells by eliminating or substantially reducing differentiated embryonic stem cells, thereby maintaining a population of undifferentiated embryonic stem cells. In addition to maintaining a substantially homogeneous population of undifferentiated embryonic stem cells by removal of any differentiating cells, it is noted that incubation of substantially homogeneous population of undifferentiated embryonic stem cells appears to suppress differentiation such that fewer cells become differentiated when incubated with the selection agent thereby selecting for undifferentiated cells. In particular embodiments of inventive methods of maintaining a population of undifferentiated embryonic stem cells, no feeder cells are used. For example, no feeder cells are used in culturing the substantially homogeneous population of undifferentiated embryonic stem cells in preferred embodiments. A preferred selection agent is an apoptosis-inducing agent, particularly a biologically active lipid second messenger such as ceramide.

Delivery of an apoptosis-inducing agent to a population of embryonic stem cells may be by various methods. In general, an apoptosis-inducing agent is added to a culture or incubation medium for embryonic stem cells to achieve a final concentration containing an amount of an apoptosis-inducing agent effective to induce apoptosis in differentiated cells. Illustratively, an effective amount is in the range of about 0.1 nanomolar-500 millimolar. An effective amount is preferably in the range of about 0.001 micromolar-500 micromolar.

The apoptosis-inducing agent may be delivered with a carrier. For example, a carrier may be used to inhibit degradation, precipitation, sequestration, and/or other forms of inactivation which reduces or prevents the apoptosis-inducing activity of the agent. Further, a carrier may be used to enhance solubility of the apoptosis-inducing agent in the medium. DMSO is an example of such a carrier. An appropriate carrier is not significantly toxic to undifferentiated cells and does not have detrimental effects on the apoptosis-inducing agent. Exemplary carriers include liquids such as buffers and solvents.

A carrier may also be a particulate carrier such as a liposome. Examples of formulations of liposomes and other particulate carriers, particularly where ceramide is included as an apoptosis-inducing agent, are described in examples herein and in U.S. Patent Application Publication No. 2005/0025820. Further examples are described in Stover T et al., J Pharmacol Exp Ther., 2003, 307:468-475; and Stover T C, et al., Clin Cancer Res., 2005, 11:3465-3474. Liposomes used in methods according to the present invention typically have particle sizes in the range of about 1 nanometer to about 1 micron, inclusive, in diameter. Nano-sized liposomes having particle sizes in the range of about 1-100 nanometers, inclusive, in diameter are preferred. In embodiments in which a liposome nanocarrier is used, the liposome has a lipid-containing wall defining an internal volume. The selection agent may be associated with the lipid containing wall. Optionally, the selection agent is associated with the internal volume.

Further particulate carriers include other nanocarriers suitable for delivering a selection agent, and particularly a lipid selection agent include but are not limited to nanospheres, nanodendrimers, nanocolloids, nanodots, nanocolumns, and combinations of these. Further description of liposomes and methods relating to their preparation and use may be found in Liposomes: A Practical Approach (The Practical Approach Series, 264), V. P. Torchilin and V. Weissig (Eds.), Oxford University Press; 2nd ed., 2003. Further description of nanocarriers may be found in S. M. Moghimi et al., Nanomedicine: current status and future prospects, FASEB J. 2005, 19, 311-30.

A selection agent may be administered to a population of cells by any of various methods. In general, a selection agent is administered to a population of cells by adding the selection agent to a medium in which the cells are cultured or passaged. The selection agent may be added to a medium in which cells are already present for instance. Alternatively, the selection agent may be added to a medium and then the combined medium and selection agent together brought into contact with cells.

Cells are incubated with a selection agent for an appropriate period of time to select for undifferentiated embryonic stem cells. The phrase "incubated with a selection agent" is intended to mean that cells are contacted with a selection agent. For example cells may be cultured substantially continuously with a selection agent, such as ceramide, to select for undifferentiated embryonic stem cells. Similarly, cells may be cultured substantially continuously with a selection agent, such as ceramide, to maintain undifferentiated embryonic stem cells in an undifferentiated state.

A method of producing and/or maintaining a desired population of cells is provided according to embodiments of the present invention which includes providing a population of embryonic stem cells heterogeneous for a characterized response to a first selection agent and incubating the population of cells with a first amount of the first selection agent effective to select a sub-population of cells having a characterized response to the first selection agent, such that a population of embryonic stem cells substantially homogeneous for a characterized response to first selection agent is obtained. The substantially homogeneous population of embryonic stem cells is then cultured in the presence of a second amount of a second selection agent effective to select a second population of cells, with the proviso that no feeder cells are used in culturing, thereby producing and maintaining a desired population of cells.

In one embodiment, the first and second selection agents comprise an apoptosis-inducing agent. Optionally, the first and second apoptosis-inducing agents are identical. For example, both the first and second apoptosis-inducing agents include a biologically active lipid second messenger in certain embodiments. Further, both the first and second apoptosis-inducing agents may include biologically active ceramide and/or a biologically active analog thereof. Where ceramide is included, the first and second amounts of biologically active ceramide are typically in the range of about 0.1-25 micromolar, inclusive.

Additionally disclosed embodiments include those in which combinations of different apoptois-inducing agents are used. For example, the first apoptosis-inducing agent may include biologically active ceramide and/or a biologically active analog thereof and the second apoptosis-inducing agent may include a non-ceramide apoptosis-inducing agent. Further embodiments include a first apoptosis-inducing agent including a non-ceramide apoptosis-inducing agent and a second apoptosis-inducing agent including biologically active ceramide and/or a biologically active analog thereof.

In additional embodiments, the first selection agent includes biologically active ceramide and the second selection agent includes a differentiation agent.

A method of producing and/or maintaining a substantially homogeneous population of embryonic stem cells derived from a first species uncontaminated by material derived from feeder cells of the same or different species is provided which includes providing a population of embryonic stem cells derived from a first species, wherein the population of embryonic stem cells is heterogeneous for sensitivity to a first apoptosis-inducing agent. The embryonic stem cells are incubated with a first amount of the first apoptosis-inducing agent effective to induce apoptosis in differentiated embryonic stem cells sensitive to the first apoptosis-inducing agent, such that a population of substantially homogeneous embryonic stem cells is obtained. The population of substantially homogeneous embryonic stem cells is then cultured in the presence of a second amount of a second apoptosis-inducing agent effective to induce apoptosis in differentiated cells sensitive to the second apoptosis-inducing agent, with the proviso that neither the population of embryonic stem cells derived from a first species nor the population of substantially homogeneous embryonic stem cells is exposed to feeder cells prior to or during culturing, thereby producing and maintaining a substantially homogeneous population of embryonic stem cells derived from a first species uncontaminated by material derived from feeder cells. The embryonic stem cells may be derived from any species. In a preferred embodiment, the embryonic stem cells are human embryonic stem cells.

A method of producing a substantially homogeneous population of embryonic stem cells derived from a first species uncontaminated by feeder cells, the feeder cells derived from a second species, is provided which includes providing a population of embryonic stem cells derived from a first species, the population of embryonic stem cells heterogeneous for sensitivity to a first apoptosis-inducing agent. The population of embryonic stem cells is incubated with a first amount of the first apoptosis-inducing agent effective to induce apoptosis in a sub-population of the population of embryonic stem cells, the sub-population sensitive to the first apoptosis-inducing agent, such that a population of substantially homogeneous embryonic stem cells is obtained, with the proviso that neither the population of embryonic stem cells derived from a first species nor the population of substantially homogeneous embryonic stem cells is exposed to feeder cells derived from a second species prior to or during culturing, thereby producing a substantially homogeneous population of embryonic stem cells derived from a first species uncontaminated by feeder cells derived from a second species.

A composition for producing a desired cell population is provided which includes a selection agent. In particular embodiments, the selection agent is associated with a nanoparticle.

A method for obtaining a substantially homogeneous population of embryonic stem cells according to the present invention includes providing a population of embryonic stem cells heterogeneous for a marker of differentiation and incubating the cells with an apoptosis-inducing agent in order to induce apoptosis in cells sensitive to the apoptosis-inducing agent. The remaining cells, resistant to the apoptosis-inducing agent are a substantially homogeneous population of undifferentiated embryonic stem cells.

Differentiation

Also provided by embodiments of methods of the present invention are methods for obtaining a substantially homogeneous population of differentiated cells. Such a method includes incubating a population of embryonic stem cells with an amount of ceramide effective to induce apoptosis in differentiated embryonic stem cells, such that a substantially homogeneous population of undifferentiated embryonic stem cells resistant to ceramide-induced apoptosis is obtained. The substantially homogeneous population of undifferentiated embryonic stem cells is then treated so as to differentiate the embryonic stem cells, resulting in a substantially homogeneous population of differentiated cells.

Any of various types of differentiated cells may be obtained by inducing differentiation of a substantially homogeneous population of embryonic stem cells produced according to methods of the present invention. Examples of such differentiated cells obtained according to methods of embodiments of the present invention illustratively include committed neuronal precursors, neurons, committed pancreatic beta cell precursors and pancreatic beta cells, bone cell precursors, bone cells, liver cell precursors, liver cells, muscle cell precursors, muscle cells, cardiac muscle precursors, cardiac muscle cells, skin cell precursors, skin cells, kidney cell precursors, kidney cells, vascular endothelial cell precursors, vascular endothelial cells, blood cell precursors, blood cells, adipose cell precursors, and adipose cells.

Elimination of differentiating cells and recruitment of homogeneous hESCs prior to differentiation in methods according to the present invention decreases the presence of precommitted endodermal and mesodermal precursor cells. This, in turn decreases the loss of cells during differentiation. Further, cell debris and cell death related molecules resulting from such cell loss is reduced, allowing more efficient production of differentiated cells.

In a preferred option, the obtained differentiated cells are substantially homogeneous for a marker of differentiation. In one embodiment, "substantially homogeneous" describes a population of cells in which more than 50% of the cells are differentiated. In a further embodiment, a substantially homogeneous population of cells is one in which more than 70% of the cells are differentiated. In another embodiment, a substantially homogeneous population of cells is one in which more than 80% of the cells are differentiated. In another embodiment, a substantially homogeneous population of cells is one in which more than 90% of the cells are differentiated. In a further embodiment, a substantially homogeneous population of cells is one in which more than 95% of the cells are differentiated. In some embodiments, a substantially homogeneous population of cells is one in which more than 99% of the cells are differentiated. Substantially homogeneous populations of hESCs are produced and differentiate into a desired cell type with higher efficiency.

A population of cells is assayed for one or more markers of differentiation to determine whether the population of cells is substantially homogeneous.

Methods of inducing differentiation in a substantially homogeneous population of embryonic stem cells include various methods such as described in Aberdam D. Derivation of keratinocyte progenitor cells and skin formation from embryonic stem cells. Int J Dev Biol. 2004 48:203-6; Bjorklund L M, Sanchez-Pernaute R, Chung S, Andersson T, Chen I Y, McNaught K S, Brownell A L, Jenkins B G, Wahlestedt C, Kim K S, Isacson O. Embryonic stem cells develop into functional dopaminergic neurons after transplantation in a Parkinson rat model. Proc Natl Acad Sci USA. 2002 99:2344-2349; Chung S, Sonntag K C, Andersson T, Bjorklund L M, Park J J, Kim D W, Kang U J, Isacson O, Kim K S. Genetic engineering of mouse embryonic stem cells by Nurr1 enhances differentiation and maturation into dopaminergic neurons. Eur J Neurosci. 2002 16:1829-1838; Kania G, Blyszczuk P, Wobus A M. The generation of insulin-producing cells from embryonic stem cells—a discussion of controversial findings. Int J Dev Biol. 2004 48:1061-4; Kawasaki H, Mizuseki K, Nishikawa S, Kaneko S, Kuwana Y, Nakanishi S, Nishikawa S I, Sasai Y. Induction of midbrain dopanminergic neurons from ES cells by stromal cell-derived inducing activity. Neuron. 2000 28:31-40; Kim J H, Auerbach J M, Rodriguez-Gomez J A, Velasco I, Gavin D, Lumelsky N, Lee S H, Nguyen J, Sanchez-Pernaute R, Bankiewicz K, McKay R. Dopamine neurons derived from embryonic stem cells function in an animal model of Parkinson's disease. Nature. 2002 418:50-6; Lee S H, Lumelsky N, Studer L, Auerbach J M, McKay R D. Efficient generation of midbrain and hindbrain neurons from mouse embryonic stem cells. Nat Biotechnol. 2000 18:675-9; Pan Y L, Cai J Y, Hu A B. Differentiation of hepatocytes from mouse embryonic stem cells and its significance. Hepatobiliary Pancreat Dis Int. 2005 4:291-4; Park C H, Minn Y K, Lee J Y, Choi D H, Chang M Y, Shim J W, Ko J Y, Koh H C, Kang M J, Kang J S, Rhie D J, Lee Y S, Son H, Moon S Y, Kim K S, Lee S H. In vitro and in vivo analyses of human embryonic stem cell-derived dopamine neurons. J Neurochem. 2005 92:1265-76; Salli U, Reddy A P, Salli N, Lu N Z, Kuo H C, Pau F K, Wolf D P, Bethea C L. Serotonin neurons derived from rhesus monkey embryonic stem cells: similarities to CNS serotonin neurons. 2004 Exp Neurol. 188:351-364; Shim J W, Koh H C, Chang M Y, Roh E, Choi C Y, Oh Y J, Son H, Lee Y S, Studer L, Lee S H. Enhanced in vitro midbrain dopamine neuron differentiation, dopaminergic function, neurite outgrowth, and 1-methyl-4-phenylpyridium resistance in mouse embryonic stem cells overexpressing Bcl-XL. J Neurosci. 2004 24:843-52; Schulz T C, Noggle S A, Palmarini G M, Weiler D A, Lyons I G, Pensa K A, Meedeniya A C, Davidson B P, Lambert N A, Condie B G. Differentiation of human embryonic stem cells to dopaminergic neurons in serum-free suspension culture. Stem Cells. 2004 22:1218-38; Schulz T C, Palmarini G M, Noggle S A, Weiler D A, Mitalipova M M, Condie B G. Directed neuronal differentiation of human embryonic stem cells. BMC Neurosci. 2003 4:27; Schuldiner M, Yanuka O, Itskovitz-Eldor J. Melton D A, Benvenisty N. Effects of eight growth factors on the differentiation of cells derived from human embryonic stem cells. Proc Natl Acad Sci USA. 2000 97:11307-12; Wichterle H, Lieberam I, Porter J A, Jessell T M. Directed differentiation of embryonic stem cells into motor neurons. Cell. 2002 110:385-97; Zeng X, Cai J, Chen J, Luo Y, You Z B, Fotter E, Wang Y, Harvey B, Miura T, Backman C, Chen G J, Rao M S, Freed W J. Dopaminergic differentiation of human embryonic stem cells. Stem Cells. 2004 22:925-40; Assady S, Maor G, Amit M, Itskovitz-Eldor J, Skorecki K L, and Tzukerman M (2001). Insulin production by human embryonic stem cells. Diabetes 50:1691-1697; Blyszczuk P, Asbrand C, Rozzo A, Kania G, St-Onge L, Rupnik M, and Wobus A M (2004). Embryonic stem cells differentiate into insulin-producing cells without selection of nestin-expressing cells. Int J Dev Biol 48:1095-1104; Blyszczuk P, Czyz J, Kania G, Wagner M, Roll U, St-Onge L, and Wobus A M (2003). Expression of Pax4 in embryonic stem cells promotes differentiation of nestin-positive progenitor and insulin-producing cells. Proc Natl Acad Sci USA 100:998-1003; Gradwohl G, Dierich A, LeMeur M, and Guillemot F (2000). neurogenin3 is required for the development of the four endocrine cell lineages of the pancreas. Proc Natl Acad Sci USA 97:1607-1611; Hori Y, Rulifson I C, Tsai B C, Heit J J, Cahoy J D, and Kim S K (2002). Growth inhibitors promote differentiation of insulin-producing tissue from embryonic stem cells. Proc Natl Acad Sci USA 99:16105-16110; Kahan B W, Jacobson L M, Hullett D A, Ochoada J M, Oberley T D, Lang K M, and Odorico J S (2003). Pancreatic precursors and differentiated islet cell types from murine embryonic stem cells: an in vitro model to study islet differentiation. Diabetes 52:2016-2024; Kitajima H, Yoshimura S, Kokuzawa J, Kato M, Iwama T, Motohashi T, Kunisada T, and Sakai N (2005). Culture method for the induction of neurospheres from mouse embryonic stem cells by coculture with PA6 stromal cells. J Neurosci Res 80:467-474; Lester L B, Kuo H C, Andrews L, Nauert B, and Wolf D P (2004). Directed differentiation of rhesus monkey ES cells into pancreatic cell phenotypes. Reprod Biol Endocrinol 2:42; Li L, Yi Z, Seno M, and Kojima I (2004). Activin A and betacellulin: effect on regeneration of pancreatic beta-cells in neonatal streptozotocin-treated rats. Diabetes 53:608-615; Lumelsky N, Blondel O, Laeng P, Velasco I, Ravin R, and McKay R (2001). Differentiation of Embryonic Stem Cells to Insulin-Secreting Structures Similar to Pancreatic Islets. Science 292:1389-1394; Miyazaki S, Yamato E, and Miyazaki Ji (2004). Regulated Expression of pdx-1 Promotes In Vitro Differentiation of Insulin-Producing Cells From Embryonic Stem Cells. Diabetes 53:1030-1037; Movassat J, Beattie G M, Lopez A D, and Hayek A (2002). Exendin 4 up-regulates expression of PDX 1 and hastens differentiation and maturation of human fetal pancreatic cells. J Clin Endocrinol Metab 87:4775-4781; Otonkoski T, Beattie G M, Mally M I, Ricordi C, and Hayek A (1993). Nicotinamide is a potent inducer of endocrine differentiation in cultured human fetal pancreatic cells. J Clin Invest 92:1459-1466; and Segev H, Fishman B, Ziskind A, Shulman M, and Itskovitz-Eldor J (2004). Differentiation of Human Embryonic Stem Cells into Insulin-Producing Clusters. Stem Cells 22:265-274.

For example, two methods of differentiating neurons include lineage selection and retinoic acid induction. In a further example, undifferentiated stem cells are treated with Activin beta-B and subsequently cultured with various factors to provide pancreatic differentiation of stem cells.

Numerous techniques are used to promote neuronal differentiation. Resulting types and ratios of the neurons differ between these approaches. Lineage selection for neuronal precursors is permissive to neuroectodermal cells and eliminates the endo- and mesodermal cells.

Derivation of neurons from hESCs may be achieved by the lineage selection method in certain embodiments. In the absence of feeder cells and bFGF, hESC colonies form embryoid bodies (EB). Subsequent culture of EBs with neurobasal medium and bFGF allows the development of neuroprogenitor cells, which are positive for neuroprogenitor markers such as nestin, Ngn-2 and Musashi-1. Upon removal of bFGF from the culture medium, these neuroprogenitor cells differentiate into neurons, positive for neuronal markers such as MAP-2.

Certain procedures for producing differentiated neurons include use of retinoic acid. Retinoic acid is believed to exert its effects by binding to cellular RA-binding proteins (CRABP) that interact with the nuclear receptors (RAR, RXR). By this mechanism, RA induces neural-specific transcription factors, which promote differentiation of GABAergic and glutaminergic neurons along with motor- and interneurons and glial cells. During selection, up to 70% of the cells—mostly mesodermal and endodermal lineages—undergo apoptosis/necrosis as described in Munoz-Sanjuan I and Brivanlou A H, Nat Rev Neurosci., 2002, 3:271-80.

Table 4 illustrates media and reagents used in exemplary neuronal differentiation methods.

TABLE 4

Neuronal Differentiation

| | Lineage Selection | Retinoic Acid Induction |
|---|---|---|
| Selection Medium | DMEM/F12 with 1% Insulin-Transferrin-Selenium (ITS), 5 micrograms/ml human plasma fibronectin. | First 7 days: DMEM/F12 5 micromolar RA |
| Extension Medium | DMEM/F12 containing 10 ng/ml bFGF, 1% N2-Supplement (insulin, transferrin, progesterone, putrescine and selenite). | 10% Replacement Serum Last 14 days: |
| Maturation Medium | DMEM/F12 containing 1% N2-Supplement, no bFGF. | DMEM/F12 10% Replacement Serum |

Derivation of nestin-positive precursors and insulin-producing (C-peptide positive) cells from substantially homogeneous populations of undifferentiated hESCs may be achieved by the lineage selection method for this cell type. A substantially homogeneous population of undifferentiated hESC cells is cultured in suspension such that colonies form embryoid bodies (EB). Subsequent culture of EBs with N2 medium allows the development of highly pure nestin-positive progenitor cells. With the addition of bFGF and nicotinamide to the culture medium, these nestin-positive cells differentiate into C-peptide positive cells, indicative of endogenous insulin production.

In a further differentiation method, a substantially homogeneous population of undifferentiated hES cells is differentiated into insulin-producing cells by culturing the substantially homogeneous population of undifferentiated hESC cells in suspension such that colonies form embryoid bodies (EB). The EBs are cultured in the presence of Activin beta-B for about 10 days, resulting in nestin-positive spheroid cell aggregates. These spheres are treated with EGF, bFGF, exendin-4 or nicotinamide for about 7 days, resulting in insulin-producing differentiated pancreatic cells.

A composition for producing a desired cell population is provided which includes a selection agent. Optionally, the selection agent is associated with a nanoparticle illustratively including but not limited to a liposome. In a further option, the selection agent includes a lipid second messenger, preferably ceramide. C6 ceramide is an illustrative example of a ceramide suitable for use in an inventive composition. Further suitable selection agents include proapoptotic agents, survival agents and differentiation agents.

Kits

A kit for producing and/or maintaining a substantially homogeneous population of undifferentiated embryonic stem cells in the absence of feeder cells is detailed herein according to embodiments of the present invention. An inventive kit includes a culture medium for embryonic stem cells and a selection agent in particular embodiments. The culture medium and selection agent may be provided in separate containers, along with instructions for mixing in certain embodiments. Alternatively, the culture medium and selection agent are provided in combination. Instructions for use of the medium and selection agent are optionally provided. A selection agent included in a kit according to embodiments of the present invention is preferably an apoptosis-inducing agent. Also preferably, the apoptosis-inducing agent includes ceramide.

A kit provided according to certain embodiments of the present invention optionally also includes a population of embryonic stem cells. The provided population of embryonic stem cells is a population of human embryonic stem cells in preferred embodiments.

In additional embodiments of a kit according to the present invention, a reagent inducing the substantially homogeneous population of undifferentiated embryonic stem cells to differentiate is included. Such a reagent may be included in a separate container and later mixed with medium or may be included in combination with the medium. A specialized culture medium for maintaining a population of differentiated cells is also optionally provided.

A kit is provided according to the present invention for producing and/or maintaining a substantially homogeneous population of undifferentiated embryonic stem cells. Such a kit includes a culture medium for embryonic stem cells and an apoptosis-inducing agent. Optionally, the culture medium and apoptosis-inducing agent are supplied as a single reagent. In a further option, the apoptosis-inducing agent includes ceramide. Also optionally, a population of undifferentiated embryonic stem cells substantially homogeneous or substantially heterogeneous for a marker of an undifferentiated state is provided in an inventive kit. Preferably, the marker of an undifferentiated state is resistance to induction of apoptosis by the apoptosis-inducing agent. Further preferably, the population of embryonic stem cells is a population of human embryonic stem cells.

A kit according to the present invention optionally includes a reagent for use in inducing the substantially homogeneous population of undifferentiated embryonic stem cells to differentiate. Illustrative examples include EGF, bFGF, exendin-4 or nicotinamide for use in producing differentiated pancreatic cells, retinoic acid for producing neurons, and bFGF for producing neuroprogenitor cells.

In a further option, a culture medium for maintaining a population of differentiated cells is supplied in an inventive kit.

In one embodiment, an apoptosis-inducing agent included in an inventive kit is associated with a liposome for delivery of the apoptosis-inducing agent to stem cells.

Substantially homogeneous populations of undifferentiated embryonic stem cells and substantially homogeneous populations of differentiated cells produced according to methods of the present invention are particularly suited for use in research, pharmaceutical agent screens and in therapeutic applications. For example, substantially homogeneous populations of cells are advantageous in research applications such as analysis of mRNAs and proteins specifically expressed in cells, since a homogeneous population provides a reduced background of "noise" from contaminating cells of other types.

Thus, substantially homogeneous populations of undifferentiated and differentiated cells of the present invention may be used to isolate mRNA, cDNA and proteins characteristic of the particular cells. Antibodies and probes may then be produced to specifically identify the cell type. Methods and reagents used in such analyses are described, for example, in J. Sambrook and D. W. Russell, Molecular Cloning: A Laboratory Manual, Cold Spring Harbor Laboratory Press; 3rd ed., 2001; F. M. Ausubel, Ed., Short Protocols in Molecular Biology, Current Protocols; 5th ed., 2002; and E. Harlow and D. Lane, Antibodies: A Laboratory Manual, Cold Spring Harbor Laboratory Press, 1988.

Substantially homogeneous populations of cells produced and/or maintained according to methods of the present invention may be used to screen for pharmaceutical agents having particular activity in relation to the cells. For example, cells may be used to assay for agents having activity as differentiation agents. Particular functions of differentiated cells may assayed to screen for enhanced or inhibited activity due to presence of particular pharmaceutical agents.

Therapeutic applications of substantially homogeneous populations of cells produced and/or maintained according to methods of the present invention include transplant into humans or animals.

Embodiments of inventive compositions and methods are illustrated in the following examples. These examples are provided for illustrative purposes and are not considered limitations on the scope of inventive compositions and methods.

EXAMPLES

Example 1

Human ES Cell Culture

NIH-registered hES cell lines, H1 (WA-01; 46XY) and H9 (WA-09; 46XX), are maintained on mouse embryonic fibroblasts (feeder cells) as recommended by the WiCell Research Institute (Madison, Wis.). Mouse feeder cells are irradiated (7500 Rad) and plated ($2\times10^4$ cells/cm$^2$) on 6-well plates pre-coated with 0.1% gelatin. Feeder cells are allowed to attach and grow overnight prior to hES cell co-culture. Human ES cells are maintained with Dulbecco's Modified Eagle Medium/F12 (Gibco) supplemented with 20% Knock-Out serum replacement (Gibco), 1% nonessential amino acids (Gibco), 2 mM GlutaMAX-1 (Gibco), 4 ng/ml basic human FGF (Invitrogen) and 0.1 mM beta-mercaptoethanol (Sigma). Cells are manually passaged following 10 min of collagenase IV incubation (1 mg/ml) at 1:5-1:10 split ratio every 5-7 days. For feeder cell-free culture, hES cells are plated and cultured on 6-well dishes coated with growth factor reduced (GFR)-MATRIGEL, diluted 1:24 in DMEM/F12. Human ES cells co-cultured with feeder cells are treated with collagenase IV for 10 min, collected manually and plated in a 1:3-1:5 split ratio (day=0). Cells are maintained with normal hES cell culture medium until treatment with ceramide (day=2). MATRIGEL is available commercially from BD Biosciences, San Jose, Calif.

Example 2

Preparation of Liposomal Ceramide

In general, delivery of ceramide via liposome is effective and characterized by minimal metabolic degradation, optimal subcellular localization and lower effective concentration compared to organic solvent-based, for example DMSO, delivery. (Stover T and Kester M., J Pharmacol Exp Ther., 2003, 307:468-475; and Stover T C, et al., Clin Cancer Res., 2005, 11:3465-3474).

Liposomal-$C_6$ is prepared as described previously (see for example, Stover et al, 2003; and Stover et al., 2005). Briefly, lipids obtained from Avanti Polar Lipids, Alabaster, Ala., are solubilized in chloroform and combined in a specific molar ratio as following: 1,2-disteoroyl-sn-glycero-3-phosphocholine (4.5); 1,2-dioleoyl-sn-glycero-3-phosphoethanolamine (2.0); 1,2-distearoyl-sn-glycero-3-phosphoethanolamine-N-[methoxy PEG(2000)] (1.0); PEG(750)-$C_8$-ceramide (0.5) and $C_6$-ceramide (2.0). The mixture is dried under a stream of nitrogen and hydrated with sterile phosphate-buffered saline solution above the lipid transition temperatures. The resulting solution is sonicated followed by extrusion through 100 nm polycarbonate membranes using the Avanti Mini Extruder (Avanti Polar Lipids, Alabaster, Ala.,). Incorporation efficiency is determined, as described in Stover T and Kester M., J Pharmacol Exp Ther., 2003, 307:468-475, by incorporating trace amounts of [$^3$H]$C_6$ into the formulation, extracting constituent lipids in chloroform/methanol (2:1), and comparing radioactivity levels of equal aliquots before and after extrusion using a scintillation counter. There is no significant loss of $C_6$ during the formulation of liposomal vesicles. This specific formulation produces pegylated nanoliposomes-containing 20 mole percent $C_6$-ceramide with an average size of 80±10 nm as measured by dynamic light scattering, as described in Stover T C, et al., Clin Cancer Res., 2005, 11:3465-3474. The composition of formulated liposomes is validated by extracting constituent lipids in chloroform/methanol (2:1) followed by resolution on preheated silica gel 60 TLC plates using a chloroform/methanol/double-distilled water (60:25:4) solvent system. Similar procedures are performed to produce liposomal formulations of other biologically active lipid second messengers, such as other biologically active ceramides, biologically active ceramide derivatives and biologically active ceramide analogs.

Example 3

Liposomal Ceramide Treatment of hES Cells

Increasing concentrations, 1, 3, 5, 10, 15 and 30 micromolar, of liposomal $C_6$-ceramide are added to hES cell culture medium after a majority of the colonies had reached a size between 0.5-0.7 mm in diameter (day 5-6 of the culture). Relative volumes of "ghost liposome" containing no ceramide are used as a control. These ghost liposomes contained an equal mass of total lipids as ceramide formulations. It is found that some effect is seen when cells are incubated with 1 micromolar ceramide, although some differentiated cells remain. Three micromolar liposomal $C_6$-ceramide is the minimally effective concentration to induce selective cell death of differentiated cells, found at the periphery of these hES cell colonies, such that 99% or more of the remaining cells are undifferentiated.

Similarly, 1, 3, 5, 10, 15 and 30 micromolar ghost or ceramide liposome concentrations are added to hES cells maintained in feeder cells-free culture system. Results show that liposomal ceramide reduces the number of differentiated cells in these feeder cell free cultures such that greater than 99% of the cells remaining in the cultures following incubation with ceramide are undifferentiated. Continued incubation of feeder cell free undifferentiated cells with ceramide is effective to maintain the undifferentiated cells in an undifferentiated state characterized by presence of markers of undifferentiated cells, including SSEA-3 and SSEA-4 and no detectable presence of markers of differentiated cells, including nestin, brachyury and alpha-fetoprotein.

The preferred effective concentrations used to eliminate differentiating stem cells are between 1 and 15 micromolar, inclusive, since these amounts effectively reduce or eliminate differentiated cells. Human embryonic stem cells undergo cell death when a concentration around 30 micromolar or higher is used. This method selectively induces apoptosis in prematurely differentiating cells expressing markers of differentiation such as nestin and beta-tubulin, well-known neuronal precursor cell markers, eliminating these cells from the cultures.

Similar procedures are performed to select undifferentiated embryonic stem cells using other biologically active lipid second messengers, such as other biologically active ceramides, biologically active ceramide derivatives and biologically active ceramide analogs.

Example 4

Liposomal Ceramide Uptake

Distribution of ceramide uptake among the hES cells within the colony is determined using liposome formulations including NBD (N-[6-[(7-nitro-2-1,3-benzoxadiazol-4-yl)amino]hexanoyl]-D-erythrosphingosine)-$C_6$ (Molecular Probes) or BODIPY FL (N-[4,4-difluoro-5,7-dimethyl-4-bora-3a,4a-diaza-s-indacene-3-pentanoyl]sphingosine)-$C_5$ (Molecular Probes) as markers of ceramide uptake, as detailed in Stover et al., 2005. On day 5 of the culture, liposomal NBD-$C_6$ or liposomal-BODIPY FL-$C_5$ is added to the culture medium for 2 hrs. At the end of the treatment period, hES cells are fixed and counterstained with Hoechst 33342 (Molecular Probes, 1:10.000 in 0.1% PBST). Liposomal ceramide uptake is evaluated using a microscopy imaging station.

The microscopy imaging station consists of an Eclipse E600 epi-fluorescence microscope with Nomarski DIC set (Nikon), 12 V/100 W halogen light source (Optical Apparatus), a CoolSnap Fx CCD camera (Photometrics), IPLab 3.9 image acquisition software (Scanalytics) and a computer with Mac operating system. This system captures high resolution images with minimal background and overlays images automatically obtained from up to three different channels. ACDSee Image Management Software 4.0 (ACDSee Systems) is used for archiving and viewing the images.

Example 5

Immunocytochemistry

Human ES cells are cultured on 22×22 mm glass cover-slips (Fisher) coated with 0.1% gelatin and mouse feeder cells. When the majority of the colonies reached the size of 0.7-0.8 mm (approximately by day 5-7), they are fixed for 30 min at 4° C. in 4% formaldehyde (Tousimis) in PBS. Immunocytochemistry is performed as described in Salli et al., 2004. Briefly, fixed cells are permeabilized by incubating with 0.5% PBST (0.5% TritonX-100 in PBS) for 5 min at room temperature (RT). Background binding is blocked by incubating the cells with freshly prepared blocking solution (0.1% PBST with 4% normal serum; Jackson ImmunoResearch Laboratories) for 30 min at RT. Subsequently, cells are incubated with the primary antibody diluted in 0.1% PBST overnight at 4° C. The antibodies and their dilutions are as follows: mouse anti-TRA-1-60, 1:100 (Chemicon), rat anti-SSEA-3, 1:100 (Chemicon); mouse anti-SSEA-4, 1:100 (Chemicon); goat anti-Oct-4, 1:50 (R&D Systems); mouse anti-nestin, 1:200 (R&D Systems); mouse anti-TUJ III, 1:200 (R&D Systems). Next, cells are incubated with either goat or donkey secondary antibodies (1:200 in 0.1% PBST) conjugated with Alexa 488 or Alexa 594 (Molecular Probes) for 1 hr at RT. Following this incubation, cell nuclei are counterstained with Hoechst 33342 (Molecular Probes, 1:10000 in 0.1% PBST) for 5 min. Glass cover-slips are mounted on 1 mm glass slides (Fisher) using a drop of Aqueous Mounting Medium (Biomeda). Resulting immunostaining is evaluated using microscopy imaging.

Example 6

Apoptosis Detection

Ceramide-induced apoptosis is assessed and visualized by TUNEL assay using the In Situ Cell Death Detection Kit, TMR Red (Roche Applied Bioscience). A TUNEL (Terminal deoxynucleotidyl Transferase Biotin-dUTP Nick End Labeling) assay measures and quantitates apoptosis by labeling DNA strand breaks in individual cells and detecting them by fluorescence microscopy. Human ES cells are cultured on glass cover-slips coated with 0.1% gelatin and mouse feeder cells. When the majority of the colonies reached the size of 0.5-0.7 mm (usually by day 5 of the culture), cells are treated with liposomal $C_6$-ceramide (3 micromolar final) or ghost (no ceramide) for 12 hr. Cells are incubated for 12 hr because cells undergoing apoptosis are still attached to the cover-slip, making observation convenient. After 12 hr, cells become round and detached. At the end of the treatment period, cells are fixed with 4% formaldehyde (Tousimis) in PBS. TUNEL assay is performed using the In Situ Cell Death Detection Kit, TMR Red (Roche Applied Bioscience) following the manufacturer's instructions. Briefly, cells are permeabilized by incubating in 0.1% PBST for 2 min on ice. TUNEL reaction mixture is prepared freshly by mixing 50 microliters of enzyme solution (terminal deoxynucleotidyl transferase) with 450 microliters label solution (nucleotide mixture). Cells are covered with 100 microliters of the reaction mixture and incubated for 60 min at 37° C. in the dark. Cells are rinsed with PBS and cover-slips are mounted on 1 mm glass slides (Fisher) using a drop of Aqueous Mounting Medium (Biomeda). Signals are visualized and acquired using a microscopy imaging station.

Example 7

Quantitative Real Time-PCR (qRT-PCR)

Total RNA is isolated from feeder cell-free cultured hES cells treated with ceramide-containing or ghost liposomes (6 samples/group; $\geqq 3 \times 10^5$ cells/sample) using the RNeasy mini kit (Qiagen). The quantity of the total RNA for each sample is measured using the NanoDrop ND-1000 Spectrophotometer (NanoDrop Technologies). The quality of the total RNA for each sample is analyzed using the Agilent 2100 Bioanalyzer with the RNA 6000 Pico LabChip in the Functional Genomic Core Facility of the Penn State College of Medicine. Complementary DNA (cDNA) is synthesized using Superscript III Reverse Transcriptase (Invitrogen). Briefly, 2 micrograms of total RNA, 500 ng oligo$(dT)_{12-18}$, and 10 mM dNTP mix are incubated for 5 min at 65° C. and chilled on ice for 1 min. Then, 5× First Strand Buffer (250 mM Tris-HCl, 375 mM KCl and 15 mM $MgCl_2$), 0.1 M DTT, 40 U RNaseOut and 200 U Superscript III RT are added. The mixture is incubated at 50° C. for 1 hr. The reaction is inactivated with a final incubation at 70° C. for 15 min. The resulting cDNA is quantified using the NanoDrop ND-1000 Spectrophotometer. Quantitative PCR is performed in a real-time detection format using TaqMan Gene Expression Assay (Applied Biosystems). Assay ID Numbers and probe sets for each primer are listed in Table 5.

TABLE 5

| Gene Name | Gene Symbol | Assay ID | Amplicon (base pair) |
|---|---|---|---|
| Acid ceramidase | ASAH1 | Hs00188842_m1 | 107 |
| Neutral ceramidase | ASAH2 | Hs00184096_m1 | 84 |
| Ceramide kinase | CERK | Hs00368483_m1 | 73 |
| Sphingosine kinase-1 | SPHK1 | Hs00184211_m1 | 62 |
| Sphingosine kinase-2 | SPHK2 | Hs00219999_m1 | 89 |
| Glucosylceramide synthase | UGCG | Hs00234293_m1 | 68 |
| Galactosylceramide synthase | UGT8 | Hs00163376_m1 | 150 |
| Glyceraldehyde-3-P dehydrogenize | GAPDH | Hs99999905_m1 | 122 |

Each TaqMan Gene Expression Assay (Assay-On-Demand) is provided in a single-tube format containing pre-designed gene-specific primers and probes. Using a 384-well plate, individual cDNA samples (40 ng) are combined with 20× TaqMan Gene Expression Assay Mix and 2×AmpErase UNG (uracil-N-glycosylase). A 7900HT ABI PRISM Sequence Detection System Instrument is used to perform and analyze qRT-PCR. Initial setup with two holds (2 min at 50° C. and 10 min 95° C.) are followed with 40 cycles (denaturing for 15 sec at 95° C. and annealing for 1 min at 60° C.). For quantification, the $2^{\Delta\Delta C_t}$ method of crossing thresholds, as described in detail in Livak et al., 2001, is performed using human GAPDH for tube-to-tube normalization. Crossing threshold is set at 5 times the standard deviation of the background. As control groups, each plate contained "No RT" (reverse transcription reaction that contained no reverse transcriptase) and "No Template" (water substituted for cDNA in the PCR reaction) to control for genomic and amplicon contamination.

Results of qRT-PCR indicating relative mRNA quantities are analyzed by paired, two-tailed Student's t-test using Graph Pad Prism v4. Mean relative expression levels of each gene (n=6) are converted to percent levels and represented as bar graphs. Results are considered significant when $P \leq 0.05$. Error bars represent S.E.M.

Example 8

Non-Liposomal Formulations of Ceramide

An exemplary non-liposomal formulation is prepared using DMSO as an organic solvent. DMSO-ceramide is prepared as 1 mM $C_6$-Ceramide solution in 1 mM BSA using 10% DMSO. Fatty-acid free bovine serum albumin (BSA) (72.6 mg) and 20 mM HEPES (pH 7.4) is mixed to 1 ml final volume in a microcentrifuge tube. 450 microliters of the BSA solution (1.1. mM) is placed into a separate microcentrifuge tube. From a 10 mg/mL stock of $C_6$-Ceramide in chloroform, 19.9 microliter solution is removed and placed into a glass conical tube. The chloroform is completely removed by drying it with nitrogen gas. Then, $C_6$-ceramide is resuspended with 50 microliters of DMSO by triturating. From this solution, a 50 microliter aliquot is removed and transferred to a tube containing 450 microliters of the BSA solution. BSA and ceramide mixture is incubated for 30 minutes at 30° C. in a shaker. The solution is vortexed or sonicated in a waterbath sonicators to clear the solution. This solution gives a 1 mM $C_6$-ceramide/BSA solution with 10% DMSO. For a vehicle control, steps above are followed except omitting ceramide.

Similar procedures are performed to formulate non-liposomal formulations of other biologically active lipid second messengers, such as other biologically active ceramides, biologically active ceramide derivatives and biologically active ceramide analogs.

Example 9

Ceramide and Non-Ceramide Formulations

Various ceramide and non-ceramide compounds are prepared as described in Example 2. For instance, $C_6$-ceramide is replaced with dihydroceramide, a biologically inactive form of ceramide and used in similar experiments, demonstrating contrasting effects of biologically active ceramides and biologically inactive ceramide. Additionally, two of the ceramide metabolites; sphingosine-1-phosphate and ceramide-1-phosphate are formulated as described in Example 2, replacing $C_6$-ceramide. hES cells are treated with liposomal sphingosine-1-phosphate in different concentrations in the range from 1 micromolar to 100 micromolar, for 6 days. During this trial period, there are no changes in cell morphology or any increase in cell death whereas ceramide treatment induced cell death selectively around the periphery of the hES cell colonies. It is expected that substitutions of biologically active ceramides with biologically inactive ceramide or ceramide metabolites will not induce apoptosis in differentiated or undifferentiated embryonic stem cells. Similarly, it is expected that substitution of other biologically active ceramides, biologically active ceramide derivatives and biologically active ceramide analogs will induce apoptosis in differentiated embryonic stem cells and not in undifferentiated embryonic stem cells.

Example 10

Long-Term Culture

The long-term effects of ceramide on hES cell immortality and their ability to differentiate into three lineages in vitro and in vivo is analyzed. In particular, karyotype, telomere length, differentiation ability at various times after treatment with ceramide in vitro (in culture dish) and in vivo (animal models) are examined. Methods and compositions of the present invention allow transition from the current standard feeder cell systems to feeder cell-free system with minimal disturbance in hES cells, avoiding heterogeneous cell populations and loss of pluripotency. Moreover, new hES cell lines can be established without any exposure to feeder cells.

For long-term culture studies, human ES cells are cultured attached on MATRIGEL, diluted 1:24 with DMEM/F-12, with normal ES medium containing 3 micromolar liposomal ceramide. Medium is changed each day. As a control, hES cells co-cultured with feeder cells are cultured under similar conditions. hES cells in feeder cell free culture system are maintained using liposomal ceramide for at least 5 passages, one passage every 5-7 days. Human ES cells in this feeder cell-free system require presence of liposomal ceramide to maintain their homogenous morphology. In the absence of ceramide their morphology changes, developing into elongated cell types. Standard stem cell markers are used to determine the developmental status of the cells cultured under all conditions.

Example 11

Undifferentiated hES cells show high levels of telomerase activity which in turn is reflected in their long telomere length. The telomere length in early passages (p30-40) is around 11 kb and stays similar (9-10 kb) in later passages (p60-70). In contrast, when hES cells differentiate, the telomerase activity decreases dramatically, telomere length shortens and cells become senescent. Compositions and methods according to the present invention are believed to be associated with high telomerase activity and long telomere length in cells cultured in accordance with inventive compositions and methods. Telomere length is determined at different time points during culture, with and without ceramide and in the presence and absence of feeder cells, by measuring terminal restriction fragment (TRF) length.

Telomere length of hES cells is measured at the beginning of the experiments and following every 15 passages, about 3-4 months. A Telo TAGGG Telomere Length Assay kit, commercially available from Roche, is used. Briefly, genomic DNA is extracted from hES cells grown with feeder cells or in ceramide-maintained feeder cell free system. Aliquots of 10 micrograms of genomic DNA are digested with Hinf I and Rsa I and digestion products are subjected to electrophoresis on a 0.5% DNA gel for Southern blot analysis. Telomere fragments are detected with telomere specific DIG-labeled probe. Telomere-probe complexes are visualized by chemiluminiscence using anti-DIG (digoxigenin) antibody. The mean TRF length is calculated based on the densitometric readings and comparison to a DNA standard on the gel. It is expected that hES cultured in the presence of ceramide will have 10-11 kb telomere length at the beginning and will continue to have same telomere length after 45 passages, typically at least 12 months in culture.

Example 12

Maintenance of normal karyotype in long-term culture of hES cells is advantageous. However, some hES cell lines exhibit karyotypic abnormalities in late passages when maintained with feeder cells. Methods and compositions according to embodiments of the present invention eliminate early differentiating cells and maintain cultures of undifferentiated cells, which may also eliminate cells having karyotypic abnormalities. Karyotyping of hES cells cultured and maintained using methods and compositions according to the present invention is performed in order to assess karyotypic abnormalities, typically every 15 passages using the standard G-banding assay. Karyotype analysis, also known as cytogenetic analysis is carried out about every 15 passages using a variety of tests. Briefly, hES cells are treated with 0.1 microgram/ml colcemid (Invitrogen) for 2 hours to induce metaphase arrest. The hES cells are dissociated with trypsin and fixed in Carnoy's solution (1 part glacial acetic acid/3 parts methanol). Standard G-banding analysis is performed at least on 50 cells in each group.

Example 13

In Vitro Differentiation

Once separated from feeder cells and serum, hES cells typically spontaneously differentiate into progenitor cells and such cultures include ectoderm, mesoderm and endoderm progenitor cells. Similar to in vivo embryogenesis, further differentiation of these progenitor cells results in formation of terminally differentiated cell types illustratively including neurons, cardiomyocytes, endothelial, and pancreatic β-cells. The ability of hES cells to form all three embryonic lineages is one of the main criteria to determine their pluripotency. Early lineage differentiation is assessed using lineage specific markers. Exemplary lineage specific markers include nestin for ectodermal; α-fetoprotein for endodermal; and brachyury for mesodermal. Later stages of differentiation of these progenitor cells into specialized cells are assessed by assay of markers for more specialized cells representing three lineages, such as serotonergic neurons, insulin-positive cells, and cardiomyocytes.

To assess in vitro differentiation, hES cells are isolated and transferred into non-coated culture plates where hES cells form embryoid bodies (EBs). For neuronal differentiation, these EBs are treated with a neurobasal medium (insulin-transferrin-selenium) to induce neuroprogenitor cell formation for seven days. Then, bFGF (10 nM) is added to medium for another seven days. Cells are fixed and subjected to ICC for neuronal cell characterization using specific antibodies for MAP2, neurofilament 160 and beta-tubulin (TUJ III). To differentiate hES cells to C-peptide positive pancreatic cells, EBs are treated with activin B for 4 days to induce endodermal lineage formation. Then, EBs are treated with exendin-4, a GLP-1 analogue, and nicotinamide for another five days. At the end of the differentiation procedure, cells are fixed and subjected to C-peptide/insulin ICC. To differentiate hES cells into cardiomyocytes, cardiomyocyte differentiation protocol is used. Briefly, EBs are cultured on laminin coated culture dishes to obtain outgrowths. These outgrowths are dissociated after two weeks of differentiation and subjected to Percoll separation. Cells in fraction IV, containing the highest percentage of cardiomyocytes, are replated in two-well plastic chamber slides (Nunc) coated with 0.5% gelatin and cultured in a medium containing 20% FBS. On the next day, cells are fixed and subjected to immunocytochemistry for cardiomyocyte markers such as sarcomeric myosin heavy chain and cardiac troponin.

Embryonic stem cells incubated with ceramide to eliminate ceramide-sensitive cells, resulting in a homogeneous population of undifferentiated embryonic stem cells are capable of differentiated into ectoderm, mesoderm or endoderm progenitor cells and further differentiation into more specialized cells. Further, a homogeneous population of embryonic stem cells produced according to embodiments of methods according to the present invention, subsequently maintained as a homogeneous population of embryonic stem cells using methods and compositions according to embodiments of the present invention are capable of differentiated into ectoderm, mesoderm or endoderm progenitor cells and further differentiation into more specialized cells.

Example 14

In vivo differentiation potential is assessed by injection of human ES cells into severe combined immunodeficient (SCID) mice and/or nude mice. Human ES cells transplanted into SCID mice and/or nude mice form complex teratomas which consist of an array of differentiated tissues representative of all three germ layers. In general, ES cells are inoculated beneath the testis or renal capsule of the animal where lesions develop about 4-6 weeks after inoculation with no gross evidence of metastatic spread to other sites within the peritoneal cavity. Some structures formed within teratomas are well organized and resemble organs (such as intestines, primitive kidney) suggesting an embryonic organogenesis performed by hES cells. It is expected that ceramide-maintained feeder cell-free hES cells form teratomas containing tissues representative of three embryonic lineages. This may be confirmed by assay for lineage specific markers, illustratively including nestin as a marker for ectodermal lineage, brachyury as a marker for mesodermal lineage, and alpha-fetoprotein as a marker for endodermal lineage.

In a specific method of assessing in vivo differentiation, approximately 3-5 million hES cells are injected into a rear leg muscle of adult male SCID mice. It is expected that palpable teratoma growth will develop about four-to-five weeks after inoculation. Thus, after about 4-5 weeks, mice are sacrificed, tissues of interest collected and fixed in Bouins overnight. Fixed tissue is sectioned according to standard procedures and counterstained with hematoxylin and eosin. Gross morphology of the tissue sections is examined using bright field light microscopy and photographed as appropriate. Tissue types present in the tetratomas are further identified using morphological identification, histochemical and/or immunochemical methods using known markers for specified cell types.

Example 15

Ceramide-Induced Cellular Response Reveals Two Distinct Subgroups of hES Cells

Various concentrations of liposomal ceramide ($C_6$), in the range of 1 to 30 micromolar, inclusive, are incubated with hES cells, H1 or H9 in this example, co-cultured with mouse feeder cells. Ceramide-induced changes are visible on a macro-scale as the hES cells rounded and detached from the colonies within 24 hr. Intriguingly and quite surprisingly, at low concentrations ($\geqq 10$ micromolar), these effects are limited solely to the cells located on the periphery of the colonies while at high concentrations (>30 micromolar), the entire hES cell colony died. Based on these observations, the peripheral hES cells are termed ceramide-sensitive (C-S) and central hES cells are termed ceramide-resistant (C-R) cells. Cells treated with ghost liposomes, that is, lipid vesicles lacking ceramide, displayed no changes regardless of the position of the cells the colony. In all subsequent experiments of this type, a three micromolar liposomal $C_6$-ceramide formulation is used, as this dose is found to be the minimum non-toxic dose that achieved selective cell killing of differentiated cells located at the periphery in these cultures.

Example 16

TUNEL assays confirm that ceramide-induced death of ceramide-sensitive cells is indeed apoptosis-mediated. No apoptotic signs among the cells in the ghost liposome-treated cells are observed, while it revealed that peripheral hES cells are undergoing apoptosis in the ceramide liposome-treated group.

Example 17

Ceramide Uptake

Unlike mouse embryonic stem (mES) cells, hES cells grow as monolayers in colonies; therefore, in theory, liposomal $C_6$-ceramide is equally available to all the cells in hES colonies. Ceramide uptake assays are performed to determine whether ceramide-sensitive and ceramide-resistant hES cell uptake liposomal ceramide equally using fluorescent-conjugated ceramide analogues, BODIPY FL-$C_5$ and NBD-$C_6$. It is found that liposomal ceramide uptake is equivalent among the cells within the colony indicating that low-dose ceramide is cytotoxic to differentiated peripheral hES cells whereas it is non-toxic for undifferentiated central cells. Uniform accumulation of these ceramide analogues in both peripheral and central hESCs indicates that apoptotic effects of ceramide on peripheral cells are not due to differential uptake or unavailability to central (non-ceramide sensitive) cells.

Example 18

Human ES Cells Expressing Signs of Premature Differentiation are Eliminated by Liposomal Ceramide Differences between ceramide-sensitive and ceramide-resistant cells are investigated. Using immunofluorescence assays for the presence of the neuroectodermal lineage markers, nestin and β-tubulin are found exclusively expressed by the peripheral hES cells suggesting that ceramide sensitivity in these cells may be due to neuroectodermal differentiation. Interestingly, immunofluorescence assays demonstrate that these ceramide-sensitive cells also express traditional stem cells markers as well, including Oct-4, TRA-1-60, SSEA-3 and SSEA-4. Cells that undergo ceramide-induced apoptosis are further assayed for nestin and β-tubulin expression. Within 24 hr of incubation with three micromolar liposomal $C_6$-ceramide hES cells expressing neuroectodermal markers were totally eliminated from cultures. Thus, although hES cell colonies appear to be uniform based on expression of commonly used stem cells markers, peripheral stem cells express neuroprogenitor markers nestin and beta-tubulin whereas centrally located stem cells do not. The peripheral location of cells expressing markers of differentiation is found to overlap with the location of ceramide-sensitive cells. Thus, liposomal ceramide has selective apoptotic effects on prematurely differentiating cells and specifically eliminates nestin-positive and beta-tubulin-positive peripheral cells in a hES co-culture system. Following incubation with ceramide, no cells are detected which express markers of differentiation, indicating that cultures are more than 99% homogeneous for undifferentiated embryonic stem cells. Similar results are demonstrated in three replicate trials.

Example 19

Liposomal Ceramide Maintains and Expands Undifferentiated hES Cells in the Absence of Feeder Cells One of the challenges to culturing hES cells in a feeder cell-free system is that some of these cells differentiate spontaneously and proliferate faster than undifferentiated cells creating a heterogeneous population that resembles the traditional feeder cell culture system, as described in Rosler, E. S. et al., Dev. Dyn. 229:259-274, 2004; Carpenter, M. K. et al., Dev. Dyn. 229:243-258, 2004; and Amit, M. et al., Biol. Reprod. 70:837-845, 2004. Success of feeder cell-free culture systems depends on suppression of premature differentiation or removal of differentiating hES cells. Here it is shown that liposomal $C_6$-ceramide eliminates differentiating hES cells in a feeder cell-free system, hES cells are plated on growth factor reduced (GFR)-MATRIGEL coated culture dishes and cultured with regular hES cell medium. These hES cells are incubated with either three micromolar ghost or three micromolar ceramide liposomes starting from the day 2 of the culture and continued for 7 days.

$C_6$-ceramide (3 micromolar) or ghost liposomes are added (t=0) to the culture medium daily. Light microscopy images of cells from 10 random fields are recorded using a Nikon TS-100 phase-contrast microscope and a Nikon CoolPix 5000 digital camera. Twenty-four hours after the treatment (t=1), approximately 35% of the cells underwent cell death and detached from the GFR-MATRIGEL, whereas remaining cells displayed healthy morphology. By day 3 (t=3), liposomal ceramide treated cells maintained their initial morphology, whereas ghost liposome treated cells displayed characteristics that resemble fibroblast cells including fast proliferation, elongation with bipolar extensions and clustering. Liposomal $C_6$-ceramide treated cells, on the other hand, maintained their initial morphology with short cytoplasmic extensions and small cytoplasmic/nuclear ratio. At day 7 (t=7), ghost-liposome treated differentiated cells covered the culture area, became multilayered and interwoven, whereas liposomal $C_6$-ceramide treated cells maintained their normal proliferation rate and morphology. Immunocytochemistry results show that cells maintained with ghost liposomes are negative for Oct-4 immunostaining, while cells maintained with ceramide liposomes are positive for Oct-4, demonstrating that hES cells are maintained in an undifferentiated state with the addition of liposomal $C_6$-ceramide to the regular hES cell culture medium. Following incubation with ceramide, no cells are detected which express markers of differentiation, indicating that cultures are more than 99% homogeneous for undifferentiated embryonic stem cells. Similar results are obtained in three replicate trials. Thus, liposomal $C_6$-ceramide efficiently maintains undifferentiated hES cells after initial elimination of differentiated cells. It is noted that regular hES cell medium is used throughout this study with no prior feeder cell conditioning or addition of growth factor cocktails.

Example 20

Elevated mRNA Expression of Genes Regulating Ceramide Metabolism in Ceramide-Resistant hES Cells In order to elucidate the mechanism(s) by which undifferentiated hES cells survive and proliferate in the presence of ceramide while differentiating cells undergo apoptosis, mRNA expression levels for genes related to ceramide metabolism are assayed in ceramide-resistant cells. The relative mean mRNA expression level of each enzyme assayed is expressed as a fraction of the basal expression following exposure to the ghost liposome group. It is found that hES cells surviving and proliferating in the presence of liposomal-ceramide express higher levels of the mRNA for the enzymes that metabolize ceramide. The mRNA for acid ceramidase, an enzyme that converts ceramide to sphingosine, is 25% higher in ceramide-resistant cells. Messenger RNA for sphingosine kinase-1 and -2, enzymes that convert sphingosine to sphingosine-1-phosphate, are 91 and 80% higher, respectively. Similarly, mRNA for ceramide kinase, which converts ceramide to ceramide-1-phosphate, is 57% higher and galactosylceramide synthase, which converts ceramide to galactosylceramide, is 37% higher in ceramide-resistant hES cells. No significant changes in the expression levels of neutral ceramidase and glucosylceramide synthase are found. Higher levels of genes expressing acid ceramidase, sphingosine kinase-1 and 2, ceramide kinase and galactosylceramide synthase suggest that ceramide-resistant hES cells efficiently metabolize exogenous $C_6$-ceramide delivered in nano-liposomes as well as endogenous physiological ceramide decreasing intracellular ceramide concentrations as well as converting ceramide to potential inducers of cell survival and proliferation such as sphingosine- or ceramide-1-phosphate. Quantitative RT-PCR results reveals that hES cells maintained in the presence of liposomal $C_6$-ceramide contain higher levels of mRNA for acid ceramidase, sphingosine kinase-1, sphingosine kinase-2 and galactosylceramide synthase. Furthermore, differentiating hES cells may be less able to metabolize ceramide, in turn, accumulating intracellular ceramide that triggers an apoptosis mechanism. Thus, culturing ceramide-resistant cells with a nano-liposomal $C_6$-ceramide delivery system leads to increased expression of gene products that metabolize ceramide to less pro-apoptotic lipid messengers.

Example 21

Increasing concentrations of dihydroceramide, a biologically inactive ceramide, are added to hES cells in parallel cultures and it is found that liposomal formulations of $C_6$-dihydroceramide had no cytotoxic effects on either ceramide-sensitive or ceramide-resistant hES cells, indicating that apoptosis induction is specifically induced by bioactive $C_6$-ceramide liposomal formulations. Similar results are demonstrated in four replicate trials.

Example 22

Effects of Ceramide on Human ESC Growth in a Mouse Feeder Cell Free System

Human ESCs are cultured on MATRIGEL coated culture dishes with or without ceramide. Without the presence of feeder cells, hESCs differentiate into fibroblast-like cells having fast growth rate, elongated morphology and characteristic nucleus/cytoplasm ratio. In contrast, addition of five micromolar ceramide to the same culture system inhibits differentiation and allows maintenance of undifferentiated stem cell growth.

Addition of ceramide to H9 (WA09) hESC-culture medium at a concentration of 5 micromolar for 8 hrs eliminates cells located on the periphery of the hESC colonies distinct in morphology from cells located towards the center of the colonies. Ceramide-sensitive cells are in contact with mouse feeder cells (MEF). Addition of vehicle alone to the medium has no significant effect on the hESCs.

A TUNEL assay reveals that hESCs on the periphery of the colonies are, indeed, undergoing apoptosis after ceramide-conditioning. Human ESCs in the group treated with vehicle alone display no difference compared to the control untreated group. Non-specific background signal, which is determined by omitting deoxynucleotidyl transferase, is undetectable.

Immunocytochemistry for stem cells markers such as SSEA-4 shows that hESCs in these cultures are immunopositive for these markers, although the cells differ in gross morphology. Human ESCs located on the periphery of the colony appear larger whereas hESCs on the center of the colony appear smaller in size. Peripheral cells are sensitive to the apoptotic effects of ceramide. Central hESCs, on the other hand, continue their normal growth after addition of ceramide to the culture medium.

Example 23

Assay for Inhibition of Cell Proliferation-[$^3$H]thymidine Incorporation into Acid-Insoluble DNA Cells are cultured in the presence of a lipid derived second messenger, derivative or analog having putative biological activity for 18 hours. Cells are then pulsed with one micro-Curie of [$^3$H]thymidine/ml of medium and incubated for six hours. Incorporation of [$^3$H]thymidine is stopped by aspiration of medium and washing cells twice with ice-cold Dubelco's phosphate-buffered saline. Cells are then fixed for one hour at 4° C. with 1 ml/well of fixing solution consisting of 40:50:10, v/v/v, water:methanol:acetic acid. A solution of 1% SDS (w/v) is applied to each well, 0.5 ml/well, for five minutes at 4° C. The SDS solution is then removed from each well and counted in a scintillation counter. Controls include addition of an aliquot of vehicle instead of the lipid derived second messenger, derivative or analog.

Example 23

Exemplary Kit

An exemplary kit according to the present invention includes a growth and/or maintenance medium for human embryonic stem cells including Dulbecco's Modified Eagle Medium/F12 (Gibco) supplemented with 20% KnockOut serum replacement (Gibco), 1% nonessential amino acids (Gibco), 2 mM GlutMAX-1 (Gibco), 4 ng/ml basic human FGF (Invitrogen) and 0.1 mM β-mercaptoethanol (Sigma). The components of the medium may be provided in separate containers for combination at about the time of use. Further included is liposomal C6-ceramide provided in a separate container. The liposomal C6-ceramide is added to the medium to achieve a final concentration in the range of about 3-25 micromolar.

Example 23

An exemplary kit according to the present invention includes a growth and/or maintenance medium for human embryonic stem cells including Dulbecco's Modified Eagle Medium/F12 (Gibco) supplemented with 20% KnockOut serum replacement (Gibco), 1% nonessential amino acids (Gibco), 2 mM GlutaMAX-1 (Gibco), 4 ng/ml basic human FGF (invitrogen) and 0.1 mM β-mercaptoethanol (Sigma). The components of the medium may be provided in separate containers for combination at about the time of use. Further included is liposomal C6-ceramide provided in a separate container. The liposomal C6-ceramide is added to the medium to achieve a final concentration in the range of about 3-25 micromolar.

An aliquot of human embryonic stem cells is provided in a separate container.

Any patents or publications mentioned in this specification are incorporated herein by reference to the same extent as if each individual publication is specifically and individually indicated to be incorporated by reference. In particular, U.S. Provisional Application No. 60/734,862, filed Nov. 9, 2005 is hereby incorporated by reference in its entirety for all purposes.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method for obtaining a substantially homogeneous population of pluripotent embryonic stem cells, comprising:
   obtaining a mixed population of cells that comprises pluripotent embryonic stem cells, and
   incubating said mixed population with an amount of C6 ceramide effective to select for pluripotent embryonic stem cells, thereby yielding a substantially homogeneous population of pluripotent embryonic stem cells,
   wherein more than 50% of the cells in the substantially homogeneous population are pluripotent embryonic stem cells.

2. The method of claim 1 wherein the embryonic stem cells are human embryonic stem cells.

3. A method for obtaining a substantially homogeneous population of pluripotent embryonic stem cells, comprising:
   obtaining a mixed population of cells comprising pluripotent embryonic stem cells and cells that have begun to undergo differentiation, and
   incubating said mixed population with an amount of C6 ceramide effective to induce apoptosis in the cells that have begun to undergo differentiation, thereby yielding a substantially homogeneous population of pluripotent embryonic stem cells,
   wherein more than 50% of the cells in the substantially homogeneous population are pluripotent embryonic stem cells.

4. The method of claim 3 wherein the embryonic stem cells are human embryonic stem cells.

5. The method of claim 3, wherein the amount of C6 ceramide effective to induce apoptosis in the cells that have begun to undergo differentiation is between about 0.1 µM and about 25 µM.

6. The method of claim 3, wherein the incubating step does not include culturing the mixed population with feeder cells.

7. A method for maintaining a population of pluripotent embryonic stem cells, comprising:
   obtaining a substantially homogeneous population of pluripotent embryonic stem cells, wherein more than 50% of the cells in the substantially homogeneous population are pluripotent embryonic stem cells, and
   culturing said substantially homogeneous population with an amount of C6 ceramide effective to select for pluripotent embryonic stem cells,
   thereby maintaining a population of pluripotent embryonic stem cells.

8. The method of claim 7, wherein the incubating step does not include culturing the mixed population with feeder cells.

* * * * *